United States Patent
Rodrigues et al.

(10) Patent No.: US 9,072,808 B2
(45) Date of Patent: *Jul. 7, 2015

(54) MULTI-SOLUTION BONE CEMENTS AND METHODS OF MAKING THE SAME

(75) Inventors: Danieli C. Rodrigues, Syracuse, NY (US); Jeremy L. Gilbert, Fayetteville, NY (US); Julie M. Hasenwinkel, Manlius, NY (US)

(73) Assignee: Syracuse University, Syracuse, NY (US)

( * ) Notice: Subject to any disclaimer, the term of this patent is extended or adjusted under 35 U.S.C. 154(b) by 795 days.

This patent is subject to a terminal disclaimer.

(21) Appl. No.: 12/372,425

(22) Filed: Feb. 17, 2009

(65) Prior Publication Data

US 2009/0239970 A1    Sep. 24, 2009

Related U.S. Application Data

(63) Continuation-in-part of application No. 11/779,025, filed on Jul. 17, 2007, now Pat. No. 8,575,274.

(60) Provisional application No. 60/807,551, filed on Jul. 17, 2006.

(51) Int. Cl.
*C08F 8/00* (2006.01)
*A61L 24/00* (2006.01)
(Continued)

(52) U.S. Cl.
CPC ........... *A61L 24/001* (2013.01); *A61B 17/7095* (2013.01); *A61F 2002/4631* (2013.01); *A61L 24/06* (2013.01); *C08F 265/06* (2013.01); *C08F 299/04* (2013.01); *A61L 2430/02* (2013.01)

(58) Field of Classification Search
CPC .................. A61L 24/001; A61L 24/06; A61F 2002/4631; C08F 265/06; C08F 220/14
USPC .......... 523/109, 115, 116, 117; 525/902, 228, 525/259, 261, 330.3, 330.5, 330.6, 302
See application file for complete search history.

(56) References Cited

U.S. PATENT DOCUMENTS 3,928,499 A    12/1975    Tomalia et al.
4,396,476 A *   8/1983    Roemer et al. ................ 522/109
(Continued)

FOREIGN PATENT DOCUMENTS

WO    WO9824398 A1    6/1998
WO    WO2006090379 A2    8/2006

OTHER PUBLICATIONS

Mendez et al. J. Biomed. Mater. Res. 2002, 61, 67-74.*
(Continued)

*Primary Examiner* — Mark Kaucher
(74) *Attorney, Agent, or Firm* — Frederick J. M. Price; George R. McGuire; Bond Schoeneck & King, PLLC

(57) ABSTRACT

The present invention relates to bone cements and, more particularly, to acrylic-based orthopedic bone cements, their use in spinal applications, and methods for making the same. An embodiment of the present invention provides multi-solution bone cements which include cross-linked PMMA beads, a linear polymer, and a monomer with various polymer to monomer ratios, and polymer bead to linear polymer ratios. The bone cement can include a polymer to monomer (P:M) ratio of between about 1:1 and 1.4:1, and can also include a polymer bead to linear polymer ratio of between about 1:1 and 2:1. Another embodiment of the present invention provides the use of a radiopacifier in the bone cement composition, such as $ZrO_2$, in increasing concentrations.

14 Claims, 18 Drawing Sheets

(51) Int. Cl.
*A61B 17/70* (2006.01)
*A61L 24/06* (2006.01)
*C08F 265/06* (2006.01)
*C08F 299/04* (2006.01)
*A61F 2/46* (2006.01)

(56) References Cited

U.S. PATENT DOCUMENTS

| | | | |
|---|---|---|---|
| 4,791,150 A * | 12/1988 | Braden et al. | 523/117 |
| 4,969,888 A | 11/1990 | Scholten et al. | |
| 5,334,626 A | 8/1994 | Lin | |
| 5,678,162 A * | 10/1997 | Barlow et al. | 419/2 |
| 5,728,583 A | 3/1998 | Kawakami et al. | |
| 5,902,839 A * | 5/1999 | Lautenschlager et al. | 523/115 |
| 5,968,999 A * | 10/1999 | Ramp et al. | 523/116 |
| 2004/0220297 A1 | 11/2004 | Bonfield et al. | |
| 2009/0239970 A1* | 9/2009 | Rodrigues et al. | 523/117 |
| 2010/0273911 A1* | 10/2010 | Hasenwinkel et al. | 523/116 |

OTHER PUBLICATIONS

Lewis, Alternative acrylic bone cement formulations for cemented arthroplasties: present status, key issues, and fracture prospects. J Biomed Mater Res B: Appl Biomater 2008, vol. 84B, pp. 301-319.
Lewis, Injectable bone cements for use in vertebroplasty and kyphoplasty: state-of-art-review. J Biomed Mater Res B: Appl Biomater 2006, vol. 76B, pp. 456-468.
Lieberman, et al., Vertebroplasty and Kyphoplasty: filler materials, Spine J 2005, vol. 5, pp. 305S-316S.
Jarvik, et al., Vertebroplasty: Learning more, but not enough, Spine 2003, vol. 28(14), pp. 1487-1489.
Belkoff, et al., Temperature measurement during polymerization of polymethylmetha-crylate cement used for vertebroplasty, Spine 2003, vol. 28(14), pp. 1555-1559.
Belkoff, et al., The biomechanics of vertebroplasty. The effect of cement volume on mechanical behavior, Spine 2001, vol. 26(14), pp. 1537-1541.
Molloy, et al., Effect of cement volume and placement on mechanical property restoration resulting from vertebroplasty, AJNR Am J Neuroradiol 2005, vol. 26, pp. 401-404.
Phillips, Minimally invasive treatments of osteoporotic vertebral compression fractures, Spine 2003, vol. 28, pp. S45-S53.
Deb, et al., The effect of cross-linking agents on acrylic bone cements containing radiopacifiers, Biomaterials 2001, vol. 22, pp. 2177-2181.
Jasper, et al., Material properties of various cements for use with vertebroplasty, J Mater Sci, Mater Med 2002, vol. 13, pp. 1-5.
Lewis, et al., Influence of the radiopacifier in an acrylic bone cement on its mechanical, thermal, and physical properties: Barium sulfate containing cement versus iodine-containing cement, J Biomed Mater Res B, Appl Biomater 2005, vol. 73B, pp. 77-87.
Van Hooy-Corstjens, et al., Mechanical behavior of a new acrylic radiopaque iodine-containing bone cement, Biomaterials 2004, vol. 25, pp. 2657-2667.
Kurtz, et al., Static and fatigue mechanical behavior of bone cement with elevated barium sulfate content for treatment of vertebral compression fractures, Biomaterials 2005 vol. 26, pp. 3699-3712.
Ginebra, et al., Mechanical performance of acrylic bone cements containing different radiopacifying agents, Biomaterials 23, 2002, pp. 1873-1882.
Wang, et al., Fracture toughness of acrylic bone cements, J Mater Science 1989, vol. 24, pp. 3725-3738.

Vallo, et al, Mechanical and fracture behavior evaluation of commercial acrylic bone cements, Polym Int 1997, vol. 43, pp. 260-268.
Persson, et al., Radiopacity of tantalum-loaded acrylic bone cement, Proc I Mech E 2006, vol. 220, pp. 787-791.
Hasenwinkel, et al., A novel high-viscosity, two-solution acrylic bone cement: effect of chemical composition on properties, J Biomed Mater Res 1999, vol. 47, pp. 36-45.
Hasenwinkel, et al., Effect of initiation chemistry on the fracture toughness, fatigue strength, and residual monomer content of a novel high-viscosity, two-solution acrylic bone cement, J Biomedical Materials Research 2002, vol. 59, pp. 411-421.
ASTM F451-99a, 2007el, "Standard Specification for Acrylic Bone Cement", ASTM International, West Conshohocken, PA, www.astm.org.
Kjellson, et al., Bone cement X-ray contrast media: A clinically relevant method of measuring their efficiency, J Biomed Mater Res B: Appl Biomater 2004, vol. 70B, pp. 354-361.
Pascual, et al., New aspects of the effect of size and size distribution on the setting parameters and mechanical properties of acrylic bone cements, Biomaterials 1996, vol. 127, pp. 509-516.
Sun, et al., Model filled polymers. VII: Flow behavior of polymers containing monodisperse crosslinked polymeric beads. Polym Eng Sci 1992, vol. 32(12), pp. 777-785.
Li, et al. Model filled polymers: The effect of particle size on the theology of filled poly(methyl methacrylate) composites. Polym Eng Sci 2004, vol. 44, pp. 452-462.
Burton, et al., Vertebroplasty and Kyphoplasty: a compressive review, Neurosurg Focus 2005, vol. 18(3), pp. 1-7.
Lewis, Properties of acrylic bone cements: State of the art review, J Biomed Mater Res B: Appl Biomater 1997, vol. 38B, pp. 155-182.
Verlan, et al., Temperature elevation after vertebroplasty with polymethyl-methacrylate in the goat spine, J Biomed Mater Res B: Appl Biomater 2003, vol. 67B, pp. 581-585.
Hass, et al., A characterization of polymethylmethacrylate bone cement, J Bone Joint Surg A 1975, vol. 57, pp. 380-391.
Meyer, et al., On the setting properties of acrylic bone cement, J Bone Joint Surg A 1973, vol. 55, pp. 149-156.
Krause, et al., The viscosity of acrylic bone cements, J Biomed Mater Res 1982, vol. 16, pp. 219-243.
Chaffey, et al., Shear thinning and thickening rheology II, Volume fraction and size of dispersed particles, J Col Interf Sci 1977, vol. 59(I), pp. 63-75.
Probstein, et al., Bimodal model of concentrated suspension viscosity for distributed particle sizes, J Rheol 1994, vol. 38(4), pp. 811-829.
Hernandez, et al., Influence of powder particle size distribution on complex viscosity and other properties of acrylic bone cement for vertebroplasty and kyphoplasty, J Biomed Mater Res B: Appl. Biomater 2006, vol. 77(B), pp. 98-103.
Borukhov I and Leibler L, Enthalic stabilization of brush coated particles in a polymer melt, Macromolecules 2002; 35: 5171-5182.
Lin EK and Gast AP, Self consistent field calculations of interactions between chains tethered to spherical interfaces. Macromolecules 1996; 29: 390-297.
Ruckenstein, Eli and Chung, Dennis Byungip, Surface Modification by a Two-Liquid Process Deposition of A-B Block Copolymers, Department of Chemical Engineering, State University of New York, Buffalo, NY, pp. 170-185.
Miller, S.T., Polymer Brushes, Science, new Series, vol. 251, No. 4996 (Feb. 22, 1991), pp. 905-914.

* cited by examiner (a)　　　(b)　　　(c)　　　(d)

MULTI-SOLUTION BONE CEMENTS AND METHODS OF MAKING THE SAME

CROSS REFERENCE TO RELATED APPLICATIONS

The present application claims priority to U.S. application Ser. No. 11/779,025, filed on Jul. 17, 2007, which claims priority to U.S. Provisional Application No. 60/807,551, filed on Jul. 17, 2006.

BACKGROUND OF THE INVENTION

1. Field of the Invention

The present invention relates to bone cements and, more particularly, to acrylic-based (i.e., the use of polymers and monomers based on methacrylic acid) orthopedic bone cements, their use in spinal applications, and methods for making the same.

2. Description of the Related Art

The clinical use of total joint replacements in the United States is expected to rise precipitously over the next twenty-five years, projected to the level of over 4 million primary total knee and hip replacement procedures performed annually by the year 2030. The number of revision surgeries for both total hips and total knees will likely double over this time period as well. Thus, the demand for high performance bone cement is rapidly growing.

One of the critical factors in the clinical success of total joint arthroplasty is stable fixation of the prosthesis; which, in a majority of cases, is accomplished through the application of PMMA-based bone cement. While bone cement has been used clinically since the early 1960's and there are many commercially available powder-liquid cement compositions, the material continues to be scrutinized for the role that it plays in aseptic loosening of total joint prostheses.

Multi-solution acrylic bone cements (typically referred to as a two-solution bone cement, but which could have more than two solutions) have surfaced as an alternative to powder-liquid cement, using the same chemical constituents as current commercial formulations. This cement consists of PMMA powder pre-dissolved in methyl methacrylate (MMA) monomer, to form two separate solutions; one containing the initiator, benzoyl peroxide (BPO) and the other containing the activator, N,N-dimethyl-p-toluidine (DMPT), which react to initiate polymerization of the MMA when the solutions are mixed. These solutions have an initial viscosity similar to that of powder-liquid cement in the dough stage, therefore they can be simultaneously mixed and delivered to the surgical site via a single, closed system. This not only simplifies the surgical procedure by eliminating the multi-stage process of cement mixing and delivery, but also reduces the extent to which the properties of the polymerized cement depend on variations in surgical technique. Two-solution bone cement compares favorably to commercial cements (Simplex P and Palacos R) both in its mechanical properties and biocompatibility.

While the two-solution bone cement concept is a promising alternative to powder-liquid cements, it has several drawbacks in its current form, primarily related to the increase in monomer concentration necessary to form viscous solutions of dissolved linear PMMA. Many important properties of the cement, including the polymerization exotherm, residual monomer concentration, volumetric shrinkage, and shrinkage-induced porosity, are directly proportional to the initial monomer concentration. These properties represent the key areas where two-solution cement currently does not perform as well as commercial powder-liquid cements. The reduction of monomer in two-solution bone cement is limited by the solution viscosity, which is controlled by both the concentration and molecular weight (MW) of the PMMA in solution. Increasing the P:M ratio, without decreasing the MW of the PMMA, increases solution viscosity, yielding cements, which are difficult to mix and deliver. Significantly decreasing the PMMA MW in order to increase the P:M ratio, however, leads to a marked decrease in the mechanical properties of the polymerized cement.

Poly (methyl methacrylate) bone cements have primarily evolved for the fixation of total hip and knee joint arthroplasties. Over 30 commercially available plain acrylic cement brands are currently approved for use in cemented arthroplasties. Some of these commercial cements have been tailored recently for the treatment of vertebral compression fractures using kyphoplasty (KP) and vertebroplasty (VP) procedures. Percutaneous VP and KP stabilize vertebral compression fractures resulting from osteoporosis and other lesions. Both procedures involve injection of modified formulations of bone cements into the fractured vertebrae in order to restore functionality and reduce pain. The desirable properties of injectable bone cements for the treatment of vertebral compression fractures (using VP and KP procedures) comprise high radiopacity, suitable viscosity to allow easy handling and injectability, high compressive strength, low curing temperature and longer setting times (e.g., about 15 minutes and mechanical properties resembling those of non-osteoporotic vertebrae). Currently, no standardized formulations meet the viscosity criteria for use in the spine. Therefore in order to lower viscosity and increase the working time of commercial cements, surgeons usually alter the polymer-to-monomer ratio recommended by manufacturers. Lower viscosities are desirable to enhance penetration of the cement into the small pores of the cancellous bone, thereby increasing the strength of the interface between bone and cement mantle. Likewise, lower exotherm temperatures may provide protection from heat damage, avoiding thermal necrosis of surrounding soft tissues. Formulations that set more slowly would allow not only extended time for heat dissipation, but also better workability and handling.

Standard two-solution bone cement (STBC, as described in U.S. Pat. No. 5,902,839) has emerged as an alternative to current powder-liquid formulations. According to studies carried out by Hasenwinkel et al (cited below) the standard two-solution cement has the advantage of being porosity free and have higher flexural strength and modulus of elasticity. One limitation of this material is the high initial viscosity of the dough, which makes injection of the cement through small needles and cannulas difficult. STBC has the advantage of presenting higher flexural strength and modulus of elasticity, being less porous than commercial formulations. It also has the advantage of being mixed in a simpler manner, which allows metered delivery of material in a closed system (see Hasenwinkel J M, Lautenschlager E P, Wixson R L, Gilbert J L, A novel high-viscosity, two-solution acrylic bone cement: effect of chemical composition on properties, J. Biomed Mater Res 1999; 47:36-45; and Hasenwinkel J M, Lautenschlager E P, Wixson R L, Gilbert J L, Effect of initiation chemisty on the fracture toughness, fatigue strength, and residual monomer content of a novel high-viscosity, two-solution acrylic bone cement, J Biomedical Materials Research 2002; 59, 411-421). However, one limitation of the use of this formulation in KP and VP is the higher initial viscosity of the cement and relatively short setting time (varying from 7 to 9 minutes from the beginning of mixing).

It is well known that acrylic bone cements are non-Newtonian or pseudoplastic fluids that undergo shear thinning with increasing shear rates, presenting significant differences in the flow behavior among compositions. The clinical significance of highly pseudoplastic cements is related to the fact that the material can be subjected to rapid thinning, which consequently enhances flow through a delivery system and into the interstices of the bone. Another important factor affecting viscosity of bone cements is the incorporation of polymer particles or fillers in the cement matrix. Polymer particle size and its distribution (polydispersity), volume fraction and particle-particle interaction are factors that determine the rheological behavior of dispersed systems. Even though the effects of the size and size distribution of PMMA particles on the properties of acrylic bone cements are discussed in the literature, most of these studies involved the application of commercial samples of linear PMMA used in powder-liquid formulations. For example, Pascual et al showed that the use of PMMA particles with average diameter in the 50-60 µm range and with wide size distribution significantly changed the maximum polymerization exotherm and setting characteristics of cement formulations (see Pascual B, Vazquez B, Gurruchaga M, Goni I, Ginebra M P, Gil F J, Planell J A, Levenfeld B, Roman J S, *New aspects of the effect of size and size distribution on the setting parameters and mechanical properties of acrylic bone cements*, Biomaterials 1996; 17:509-516). Likewise, Hernandez et al discussed the influence of powder size distribution on the properties of cements used in KP and VP showing that cements with a high proportion of large PMMA beads (~118 µm) to small beads (~70 µm) presented suitable viscosity behavior and injectability (see Hernandez L, Gurruchaga M, Goni I, *Influence of powder particle size distribution on complex viscosity and other properties of acrylic bone cement for vertebroplasty and kyphoplasty*, J Biomed Mater Res B: Appl Biomater 2006; 77B:98-103).

The application of acrylic bone cement for the treatment of vertebral compression fractures requires visualization of the material flow under image fluoroscopy. In order to enhance contrast, it is common practice to alter the composition of commercial cements by increasing the amount of radiopacifier. Radiopacity of the cements is achieved by the addition of contrast radiopacifier materials, such as $BaSO_4$ and $ZrO_2$, which are vastly discussed in the literature to cause alterations in the biological and mechanical properties of cements. The effect of $BaSO_4$ on the static and dynamic properties of bone cements is somewhat contradictory. Most studies have reported deleterious effects of $BaSO_4$ in the mechanical performance of cements due to clumping resulting from the heterogeneity and incompatibility of the polymeric matrix and inorganic salt. For example, Wang et al pointed out that the addition of $BaSO_4$ to Simplex P lowers the ultimate tensile strength and fracture toughness of the material (see Wang C T, Pilliar R M, *Fracture toughness of acrylic bone cements*, J Mater Sci 1989; 24:3725-38). Ginebra et al showed a similar trend in tensile strength by the presence of $BaSO_4$ in comparison to a radiolucent cement (see Ginebra M P, Albuixech L, Fernandez-Barragan E, Aparicio C, Gil F J, San Roman J, Vazquez B, Planell J A, *Mechanical performance of acrylic bone cements containing different radiopacifying agents*, Biomaterials 23; 2002:1873-1882). On the contrary, Kurtz et al and Jasper et al reported a significant increase in the compressive properties as a function of increasing $BaSO_4$ content (see Kurtz S M, Villarraga M L, Zhao K, Edidin A A, *Static and fatigue mechanical behavior of bone cement with elevated barium sulfate content for treatment of vertebral compression fractures*, Biomaterials 2005; 26:3699-3712; Jasper L E, Deramond H, Mathis J M, Belkoff S M, *Material properties of various cements for use with vertebroplasty*, J Mater Sci: Mater Med 2002; 13:1-5). Vallo et al reported that the presence of radiopacifier fillers improved fracture toughness by promoting interactions between the crack and the second phase dispersion, and Deb el al concluded that the presence of the inorganic phase did not seem to affect the tensile strength of acrylic cements (see Vallo C I, Cuadrado T R, Frontine P M, *Mechanical and fracture behavior evaluation of commercial acrylic bone cements*, Polym Int 1997; 43:260-268; Deb B and Vazquez B, *The effect of cross-linking agents on acrylic bone cements containing radiopacifiers*, Biomaterials 2001; 22:2177-2181). In view of these contradictory opinions, alternative radiopacifiers and methods have been explored, as for example, the use of tantalum-based cements, iodine containing monomers and substitution of $ZrO_2$ for $BaSO_4$, which seems to have less detrimental effects due to the size and morphology of the particles that allow for better adhesion within the matrix. Current commercial cements that utilize ZrO2 include Palacos R (Zimmer, Inc.).

Description Of the Related Art Section Disclaimer: To the extent that specific publications are discussed above in this Description of the Related Art Section, these discussions should not be taken as an admission that the discussed publications are prior art for patent law purposes. For example, some or all of the discussed publications may not be sufficiently early in time, may not reflect subject matter developed early enough in time and/or may not be sufficiently enabling so as to amount to prior art for patent law purposes. To the extent that specific publications are discussed above in this Description of the Related Art Section (as well as throughout the application), they are all hereby incorporated by reference into this document in their respective entirety(ies).

SUMMARY OF THE INVENTION

It is therefore a principal object and advantage of the present invention to provide a multi-solution bone cement incorporating more PMMA.

It is another object and advantage of the present invention to provide a multi-solution bone cement having improved mechanical properties.

The viscosity and setting parameters of acrylic bone cements used for restoring vertebral compression fractures are critical factors in VP and KP procedures. Thus, it is another object and advantage of the present invention to provide a multi-solution bone cement which exhibits lower viscosities to allow easy handling and injectability, high compressive strength, low curing temperature and longer setting times. This object and advantage is designed to overcome the difficulty of forcing the "dough" through small needles upon application, and to reduce the risk of cementing the multi-solution bone cement during surgery.

It is a further object and advantage of the present invention to provide a multi-solution bone cement which exhibits high radiopacity.

In accordance with the foregoing objects and advantages, an embodiment of the present invention provides multi-solution bone cements which include cross-linked PMMA beads, thereby providing for a significant increase in the polymer-to-monomer (P:M) ratio. As a result, the bone cements of the present invention have reduced polymerization exotherms, volumetric shrinkage, shrinkage induced porosity, and residual monomer, all of which are advantageous for the clinical performance of the cement. When surface modified with unsaturated carbon double bonds, the cross-linked PMMA beads exhibit improved interfacial adhesion between the beads and the polymerized cement matrix by allowing them to participate in the polymerization reaction and thus be covalently bound to the matrix, thereby improving the mechanical properties of cements made with functionalized beads. One advantage of the multi-solution bone cements of the present invention is the ability to adjust viscosity by means of the P:M ratio and the ratio of cross-linked beads to linear polymer in the composition.

In accordance with an embodiment of the present invention, the present invention also comprises multi-solution bone cements made with PMMA-PMMA spherical brush polymers. The density and molecular weight of PMMA chains grafted onto cross-linked PMMA beads are controlled through the atom transfer radical polymerization process, along with the concentration of these particles in the monomer solutions, thereby enabling the manufacture of bone cements with tailored viscosities.

As noted supra, multi-solution bone cements consist of linear polymer chains consisting of acrylate (e.g., PMMA) polymer dissolved into MMA monomer. The viscosity of these cements is dictated by the combination of polymer molecular weight and polymer-to-monomer ratio. Increasing either of these quantities will increase the viscosity. In order to obtain workable cement viscosities, the combination of suitable molecular weight and polymer to monomer ratio are typically in the 80,000 g/mol lower limit Mw and about 0.95:1 polymer-to-monomer ratio. Since typical powder liquid cements are in the range of 1.8:1 P:M ratio, changes in two solution cement are needed to raise the P:M ratio while still preserving suitable viscosity.

In accordance with an embodiment of the present invention, modified multi-solution cements contain an additional element that can comprise either cross-linked PMMA beads or reactive cross-linked beads (where reactive double bond groups are placed on the surface of the beads) that are added to the multi solution mixture. The amount of crosslinking within the beads, the ratio of linear polymer (Pl) to bead-based polymer (Pb), and the bead size will all affect the viscosity of the mixture. Furthermore, varying crosslinking concentration (i.e., the amount of crosslinking agent used to create the cross-linked PMMA beads—e.g., EGDMA) within the polymer beads will affect the amount of monomer uptake and swelling that can take place within the beads which will, in turn, affect the overall viscosity of the system. Additionally, cements can be made by the addition of spherical polymer brushes alone to MMA.

In addition to the advantages previously described, the bone cements of an embodiment of the present invention are significantly simpler for the surgeon to mix and apply in the operating room compared to current powder-liquid bone cements. Simplification of this process eliminates much of the technique-dependent variability in bone cement properties. Additionally, the polymerization of multi-solution based bone cements is initiated by mixing the two or more components through a static mixing nozzle (current design) or some comparable device. The cement can be simultaneously mixed and delivered to the surgical site of application if desired. The use of a disposable mixing nozzle allows for metered dosing from a single batch of cement. For example, a desired volume of material can be mixed and delivered in order to cement the first component of a total knee replacement. The mixing nozzle can then be removed and at the appropriate time, a new nozzle can be attached to mix the cement for the second component of the knee implant. The flexibility that this type of approach affords the surgeon is highly advantageous from a delivery standpoint because it allows for multiple cement applications at different times during a single surgical procedure, from a single batch or dose of cement. This type of approach is not possible with conventional bone cements because an entire batch must be mixed at one time, thus starting the polymerization reaction and limiting the time with which the surgeon can work with the cement before it cures. Bone cements of different viscosities are desirable for different surgical procedures (e.g., khyphoplasty vs. total hip cementation vs. total knee cementation). The ability to customize cements for the various market niches within the field of orthopedics is therefore highly desirable.

In accordance with an additional embodiment of the present invention, the viscosity of standard two-solution bone cement (STSBC) can be manipulated by subtle changes in the polymer-to-monomer ratio and by the incorporation of cross-linked poly (methyl methacrylate) PMMA microspheres or nanospheres in the polymer phase. In a preferred embodiment, addition cross-linked PMMA particles can be added at specific ratios, e.g., in the 20-100 μm and 300-330 nm size-range (which was evaluated on the rheological properties and setting behavior of novel multi-solution cements, as discussed in the Examples below). The addition of the cross-linked PMMA particles was observed to reduce the initial viscosity in comparison to the standard formulation, and to improve the setting properties of multi-solution cements by increasing setting time and reducing maximum exotherm significantly.

In accordance with an additional embodiment of the present invention, the material properties of multi-solution bone cements of an embodiment of the present invention composed of cross-linked poly (methyl methacrylate) PMMA microspheres or nanospheres added to the linear polymer phase at a fixed ratio were assessed for formulations with increasing concentrations of zirconium dioxide ($ZrO_2$). The optical density was measured for three-cement formulations (standard two-solution containing linear PMMA (STSBC), modified two-solution containing cross-linked PMMA microspheres and modified cement containing cross-linked PMMA nanospheres) and compared to KyphX HV-R containing 30% barium sulfate ($BaSO_4$). Static compression testing was performed with formulations containing 0, 5, 20 and 30% $ZrO_2$. As discussed in the Examples section infra, cements prepared with cross-linked beads exhibited significantly higher compressive strength ($p<0.05$) than standard-two solution cement at increasing radiopacifier concentrations and significantly higher compressive strength ($p<0.05$) than KyphX. The strength of these bone cement formulations increased with increasing concentration of radiopacifier. In contrast, the addition of higher amounts of radiopacifier to the standard two-solution cement composition had a detrimental effect on the measured properties of the material. Cements containing cross-linked PMMA particles exhibited matrices with even dispersion of radiopacifier and reduced porosity in comparison to KyphX and standard two-solution formulations. Furthermore, cement viscosity was increased by the addition of increasing concentrations of radiopacifier in the modified two-solution cements, while the maximum polymerization exotherm and setting time of these materials were decreased. The results indicate that the addition of high concentrations of $ZrO_2$ significantly affects the properties of two-solution bone cements acting as a reinforcing phase when cross-linked spheres are added to the cement solution. These materials were observed to be suitable for vertebroplasty applications.

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 1:
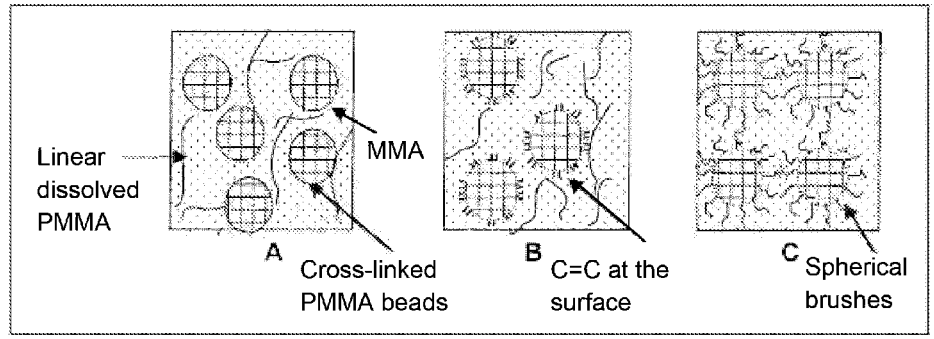
FIG. 1 is a schematic of three bone cement systems according to an embodiment of the present invention.

Referring now to the drawings, wherein like reference numerals refer to like parts throughout, there is seen in FIG. 1 (FIG. 1 A-C) three cement systems according to the present invention. Briefly, FIG. 1(A) shows linear polymer and cross-linked beads in monomer, FIG. 1(B) shows linear polymer, and C=C modified cross-linked beads in monomer, and FIG. 1(C) shows polymer brushes in monomer.

An embodiment of the present invention generally comprises multi-solution based bone cements having polymer-to-monomer (P:M) ratios approaching 2:1 and material properties that are comparable to currently available powder-liquid cements.

In accordance with an embodiment of the present invention, the viscosity of the cement solutions of the present invention are a function of the total P:M ratio, the ratio of cross-linked beads to linear polymer, and the cross-link density and size of the beads. The bone cements of an embodiment of the present invention are formed by adding polymer in the form of cross-linked poly(methyl methacrylate) (PMMA) beads to solutions of dissolved linear polymer. Alternatively, the present invention is formed by replacing the linear polymer with spherical PMMA brushes. Cross-linked PMMA particles swell in monomer but do not dissolve, minimizing their contribution to the viscosity of the polymer solutions compared to the dissolved linear polymer.

An embodiment of the present invention involves the enhancement of the interfacial bonding of this particle phase to the polymerized PMMA matrix, and subsequently the mechanical properties of the cement, by creating reactive sites at the surface of the cross-linked beads that could participate in the free radical polymerization reaction during cement curing.

An embodiment of the present invention also encompasses the synthesis of spherical polymer brushes, consisting of cross-linked PMMA beads with linear PMMA molecules covalently tethered to their surfaces. The spherical PMMA are mixed with methyl methacrylate (MMA) monomer to create bone cement formulations which do not required additional dissolved linear PMMA. In the presence of the monomer, the cross-linked bead component of the spherical brushes will swell and the tethered PMMA chains will act like dissolved polymer, although anchored at one end, thereby imparting both viscosity to the mixtures through physical chain entanglements and a mechanically coupled interface at the surface of the beads.

In accordance with an embodiment of the present invention, plain cross-linked PMMA beads can be used in combination with dissolved linear PMMA in methyl methacrylate monomer (MMA) to form the first cement type, as seen in FIG. 1(A).

In accordance with an embodiment of the present invention, the cross-linked PMMA beads can be modified via chemical reaction, in order to create functional reactive sites at the surface of the beads, consisting of carbon-carbon double bonds. These bonds will be able to participate in the free radical polymerization reaction that occurs during bone cement setting, creating a covalent or chemical bond between the cross-linked beads and the polymerized cement matrix. These cross-linked PMMA beads can be used in combination with dissolved linear PMMA in MMA monomer to form the second cement type, as seen in FIG. 1(B). Using functionalized beads in this cement composition improves interfacial bonding between the particle phase and the polymerized PMMA matrix, resulting in cements with enhanced mechanical properties.

In accordance with an embodiment of the present invention, the last cement type is based on the synthesis of spherical polymer brushes, consisting of cross-linked PMMA beads with linear PMMA molecules covalently tethered to their surfaces. Spherical PMMA brushes are then be mixed with methyl methacrylate (MMA) monomer to create the third cement type, as seen in FIG. 1(C). This cement composition does not require additional dissolved linear PMMA. In the presence of the monomer, the cross-linked bead component of the spherical brushes will swell and the tethered PMMA chains will act like dissolved polymer, although anchored at one end, thereby imparting both viscosity to the mixture through physical chain entanglements and a mechanically coupled interface at the surface of the beads.

Advantages of the invention are illustrated by the following Examples. However, the particular materials and amounts thereof recited in these examples, as well as other conditions and details, are to be interpreted to apply broadly in the art and should not be construed to unduly restrict or limit the invention in any way.

EXAMPLES

Example 1

Synthesis of Cross-linked PMMA Beads

This example relates to the synthesis of cross-linked PMMA beads. In brief, cross-linked PMMA beads have been synthesized via suspension polymerization of methyl methacrylate, using benzoyl peroxide (BPO), 2,2'-azo-bis-isobutyrylnitrile (AIBN), or potassium persulfate (KPS) as the initiator, ethylene glycol dimethacrylate (EGDMA) as the cross-linker (in varying concentrations), and poly(vinyl alcohol) (PVA) as the stabilizer. Resulting beads were subjected to post-synthesis heat treatment at 91° C. for 18 h in order to decompose any residual BPO and yield polymer that is stable in monomer solutions containing DMPT. Bead size can be controlled by varying the suspension medium and the speed of mixing during the synthesis. Beads that have been synthesized to date range in size from less than 1 µm to over 100 µm in diameter, with the majority in the 10-50 µm range. Cross-linker concentrations have been varied between 1% and 30%. The degree to which the beads swell in monomer solutions is inversely proportional to the cross-linker concentration used in the synthesis.

Example 2

Preparation of Multi-solution Based Bone Cement with Cross-linked PMMA Beads

This example relates to the preparation of multi-solution based bone cement with cross-linked PMMA beads as synthesized in Example 1. First, the desired ratio of cross-linked beads to PMMA powder (linear chains) is determined. These two components are massed and subsequently mixed together in a suitable container. Next, MMA is added to two graduated cylinders. The desired concentrations of BPO initiator or DMPT activator are then dissolved in MMA in separate containers, followed by the addition of 10-30 wt % barium sulfate (if radiopacity is desired, e.g., for vertebroplasty and kyphoplasty applications). The solutions are transferred to polypropylene cartridges. Next, the mixture of PMMA powder and cross-linked PMMA beads is added to the MMA solutions. The cartridges are sealed, vigorously agitated by hand, and placed on a rotating drum mixer for 6 hours. This is a significant reduction in mixing time as compared to current two-solution cement formulations without cross-linked beads (18 hr). Following mixing, the cartridges are removed and stored upright at 4° C. The solutions can be mixed through a static mixing nozzle and polymerize in the same manner as two-solution bone cement without cross-linked beads.

Example 3

Properties of Multi-solution Based Bone Cement with Cross-linked PMMA Beads

Figure 2:
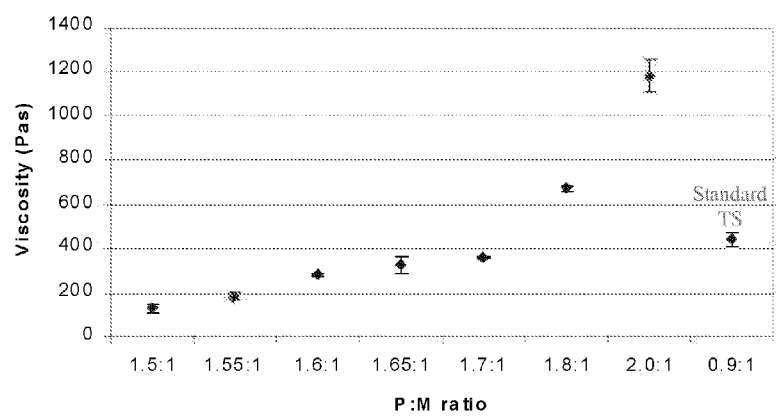
FIG. 2 is a graph of viscosity versus polymer-to-monomer ratios for multi-solution bone cements according to an embodiment of the present invention.

This example relates to the properties of the multi solution based bone cement with cross-linked PMMA beads as described in Example 2. A number of experiments have been performed to characterize the properties of solutions and potential cement compositions of multi-solution based bone cement with cross-linked PMMA beads. The viscosity of solutions consisting of cross-linked PMMA beads, linear PMMA, and MMA, increase significantly with increasing polymer-to-monomer (P:M) ratio, as seen in FIG. 2. FIG. 2 depicts the viscosity versus polymer-to-monomer ratio for multi-solution based bone cements with cross-linked PMMA beads. Solutions had a constant ratio in the concentration of cross-linked beads to linear PMMA. As expected, viscosity increases significantly with increasing P:M ratio. The addition of cross-linked PMMA beads allows for a nearly double P:M ratio compared to standard two-solution (TS) cements with comparable solution viscosity. The viscosity of Simplex P commercial bone cement has been reported as 800 Pa*s at 3 min after the onset of mixing. This data also demonstrates that the P:M ratio of these cements can be nearly doubled as compared to standard two-solution cements, while maintaining a comparable viscosity.

The polymerization exotherm measured for multi-solution bone cement with cross-linked PMMA beads was significantly lower than that of standard two-solution cement with the same initiation chemistry and comparable to the commercially available Palacos R-40 bone cement. There were no significant differences in setting times across the three compositions. These data are for a single cement composition with a P:M ratio of 1.4:1. The polymerization exotherm in setting bone cement is inversely proportional to the P:M ratio, therefore, it is reasonable to expect that a further reduction in exotherm could be achieved by increasing the P:M ratio to the range of 1.7:1, which is certainly feasible from a viscosity standpoint, see FIG. 2.

Table 1 below provides the exotherm and setting time for multi-solution based cement with cross-linked beads, standard two-solution cement, and Palacos R-40 commercial cement. Values are given as the average one standard deviation and significant differences (p <0.05) are denoted by asterisks.

TABLE 1

|  |  | Palacos R-40 | Two-solution | multi-solution w/beads | |
|---|---|---|---|---|---|
| P:M | $P_b:P_l$ | 1.71:1 | 0.9:1 | 1.4:1 | 1.8:1 |
| $T_{max}$ (° C.) | | 81.18 ± 5.99 | 95.012 ± 5.75* | 75.97 ± 0.94 | |
| $t_{set}$ (min) | | 8.48 ± 0.31 | 8.73 ± 0.52 | 9.175 ± 0.12 | |

Figure 3:
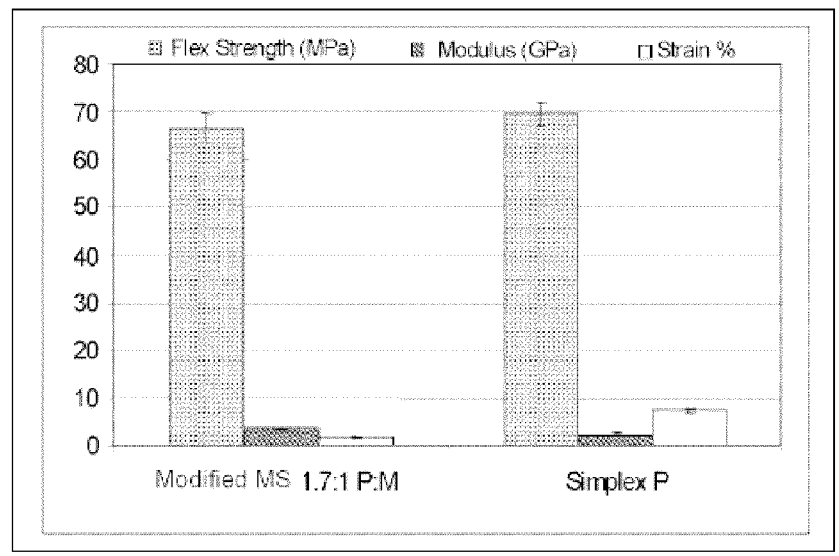
FIG. 3 is a graph of flexural testing data for multi-solution bone cements according to an embodiment of the present invention.

As seen in FIG. 3, in a preliminary investigation of the flexural mechanical properties of multi-solution based bone cements with cross-linked PMMA beads, this type of cement displays comparable flexural strength to Simplex P bone cement. FIG. 3 provides flexural testing data showing flexural strength, modulus, and strain-to-failure for one composition of multi-solution based bone cement with cross-linked PMMA beads at a P:M ratio of 1.7:1 and Simplex P bone cement. There is a significant reduction in the strain-to-failure for the multi-solution based cement.

Figure 4:
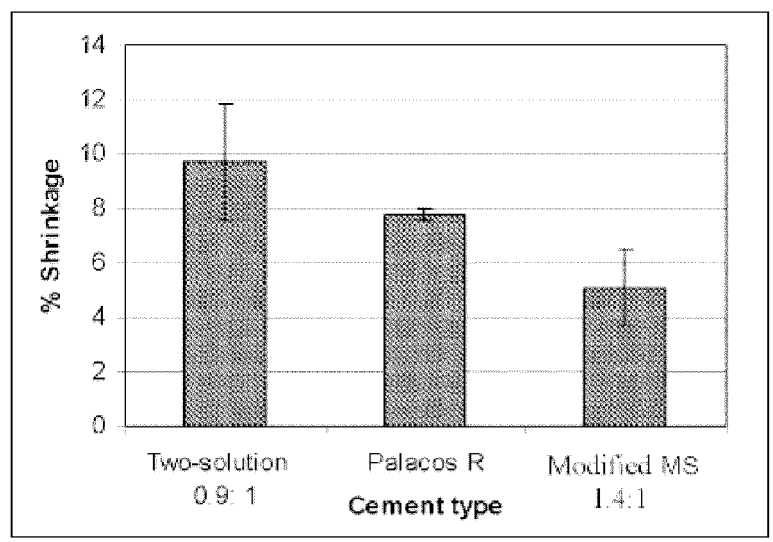
FIG. 4 is graph of volumetric shrinkage verses bone cement composition according to an embodiment of the present invention.

Referring to FIG. 4, tests measuring the volumetric shrinkage of bone cement during the polymerization process show that multi-solution based bone cement with cross-linked PMMA beads at a P:M ratio of 1.4:1 had significantly reduced shrinkage versus standard two-solution cement and Palacos R-40 bone cement. FIG. 4 depicts volumetric shrinkage versus cement composition. Increasing the P:M ratio of multi-solution bone cement via the addition of cross-linked PMMA beads reduced the volumetric shrinkage of the cement, which is due to the conversion of monomer to polymer. This data demonstrates another cement property for which an increase in the P:M ratio is beneficial.

Example 4

Surface Modification of PMMA Cross-linked Beads

This example relates to the surface modification of PMMA cross-linked beads as synthesized in Example 1. The bead-matrix interface can be mechanically strengthened by promoting covalent bonding between the two phases. Therefore, cross-linked PMMA beads have been modified to create unsaturated carbon double bonds at their surface. These double bonds can participate in the free radical polymerization reaction during matrix formation, potentially creating a chemical bond at the bead-matrix interface.

Step One: Surface Modification of PMMA Beads with Ethanolamine

Figure 5:
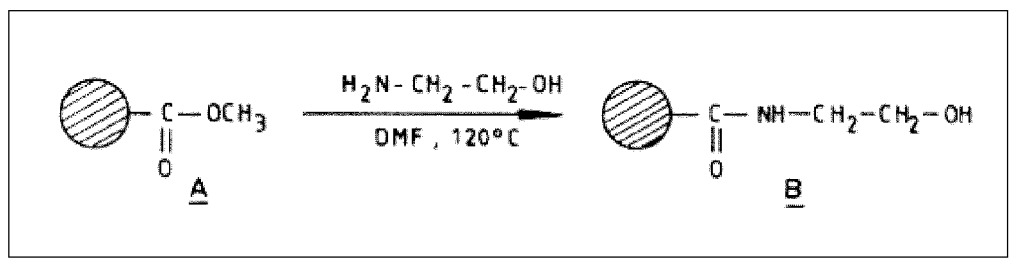
FIG. 5 is a reaction schematic of PMMA with ethanolamine in DMF according to an embodiment of the present invention.
Figure 6:
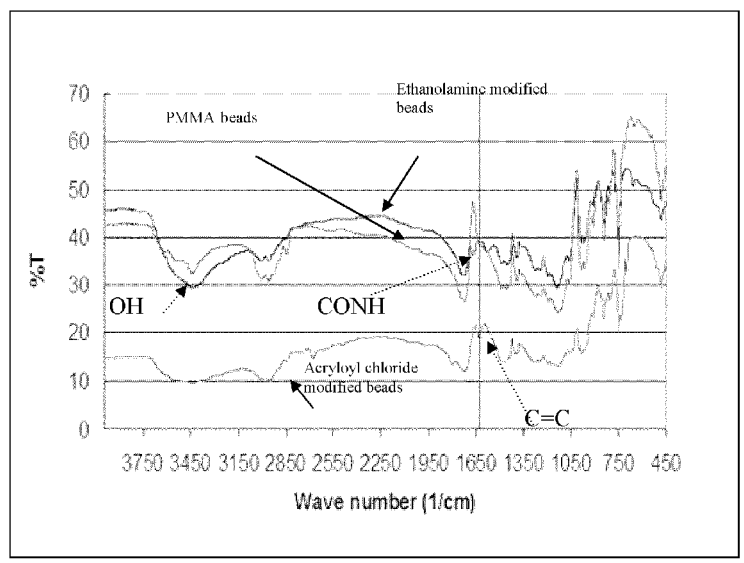
FIG. 6 is a graph of FTIR profiles in transmission mode of the modification reactions according to an embodiment of the present invention.

The first step in the formation of modified PMMA beads according to the invention is to modify the surface of PMMA beads by adding a hydroxyl group. This reaction replaces the ester group with a hydroxyl group, as shown in FIG. 5. The reaction was performed at 120° C. in N,N dimethylformamide (DMF). Twenty grams of cross-linked PMMA beads were swollen for 12 hours in DMF. Then the beads were subjected to a reaction with 25 g of ethanolamine at 120° C. for 9 hours. The reaction was then cooled to ambient temperature. The beads were washed with water, followed by methanol. Finally, the beads were subjected to soxhlet extraction with methanol for 48 hours to extract any ethanolamine residue. FTIR analysis of the beads was performed by incorporating the modified beads in a potassium bromide (KBr) pellet. FIG. 6 contains three lines starting from the left (related to each other relative to the vertical axis) including a "top," "middle," and "bottom" line or spectrum. FIG. 6 illustrates the FTIR spectra of cross-linked PMMA beads (middle spectrum) and ethanolamine surface modified PMMA beads (top spectrum). FIG. 6 details the FTIR profiles in transmission mode of the two step modification reactions. The middle line shows the spectrum of the unmodified cross-linked PMMA beads. The top line shows the spectrum of ethanolamine modifies beads. The bottom line shows the spectrum of acryloyl modified beads. Note the carbon-carbon double bond peak at ≈1640 cm$^{-1}$. The hydroxyl group is very clear at 3450 cm and amide group at 1680 cm$^{-1}$. These two peaks increase in intensity with increasing reaction time or decreasing cross-linker concentration.

Step Two: Surface Modification with Acryloyl Chloride

Figure 7:
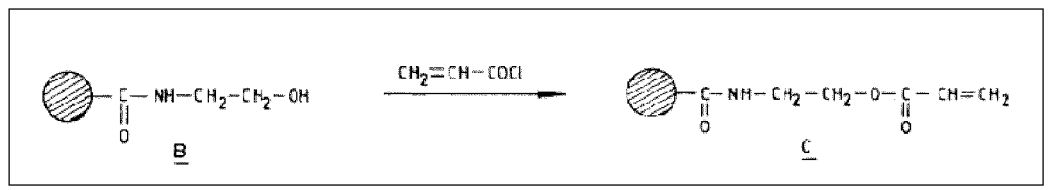
FIG. 7 is a reaction schematic of modified PMMA beads with acryloyl chloride in dimchloromethane according to an embodiment of the present invention.

The second step in the formation of modified PMMA beads according to the invention is to subject the ethanolamine modified cross-linked PMMA beads to acryloyl chloride in dry dichloromethane in the presence of triethylamine, as seen in FIG. 7. Five grams of cross-linked PMMA beads were swollen in 25 g of dry dichloromethane and cooled on ice under stirring. The reaction was permitted to go for 6 hours at 0° C. and then for another 6 hours at room temperature. The product was then washed with 0.1 N HCl followed by saturated sodium hydrogen carbonate solution, followed by water, and finally methanol. The product was dried in a vacuum at room temperature. FIG. 6 shows the FTIR spectrum of acryloyl chloride modified beads (bottom line) in KBR pallets. Note the drop in the hydroxyl peak at 3450 cm$^{-1}$ and the formation of the carbon-carbon double bond peak at 1640 cm$^{-1}$.

Example 5

Preparation of Multi-solution Bone Cement with Surface Modified PMMA Beads

This Example relates to the preparation of multi-solution bone cement with the surface modified PMMA as synthesized in Example 4. The formation of modified PMMA beads according to the invention also requires determining the desired ratio of surface modified, cross-linked beads to PMMA powder (linear chains). These two components are massed and subsequently mixed together in a suitable container. Next, MMA is added to two graduated cylinders. The desired concentration of BPO initiator or DMPT activator is then dissolved in the MMA, followed by the addition of 10-30 wt % barium sulfate (if radiopacity is desired). The solutions are transferred to 200 ml polypropylene cartridges. Next, the mixture of PMMA powder and surface modified, cross-linked PMMA beads is added to the MMA solutions. The cartridges are sealed, vigorously agitated by hand, and placed on a rotating drum mixer for 6 hours. Following mixing, the cartridges are removed and stored upright at 4° C. The solutions can be mixed through a static mixing nozzle and polymerize in the same manner as multi-solution bone cement without cross-linked beads.

Example 6

Synthesis of PMMA-PMMA Spherical Polymer Brushes

Figure 8:
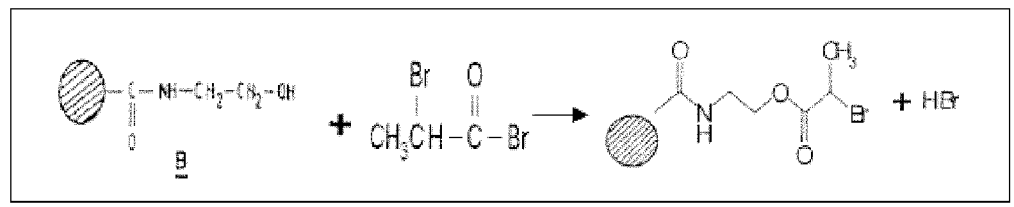
FIG. 8 is a reaction schematic of a modification reaction according to an embodiment of the present invention.

This Example relates to the synthesis of PMMA-PMMA spherical polymer brushes. The synthesis of the polymer brushes of the present invention is performed by surface modification of PMMA beads with ethanolamine as previously described in Example 4, followed by modification with 2-bromoisobutyryl bromide and finally an atom transfer radical polymerization (ATRP) reaction with MMA. Surface modification with 2-bromoisobutyryl bromide was performed on ethanolamine modified PMMA beads in THF at 0° C. in the presence of triethylamine for 12 hrs. This reaction was continued for 24 hours at room temperature followed by filtrations, cleaning and finally drying in a vacuum at room temperature. FIG. 8 is a schematic of the reaction between ethanolamine modified PMMA beads and 2-bromoisobutyryl bromide.

Figure 9:
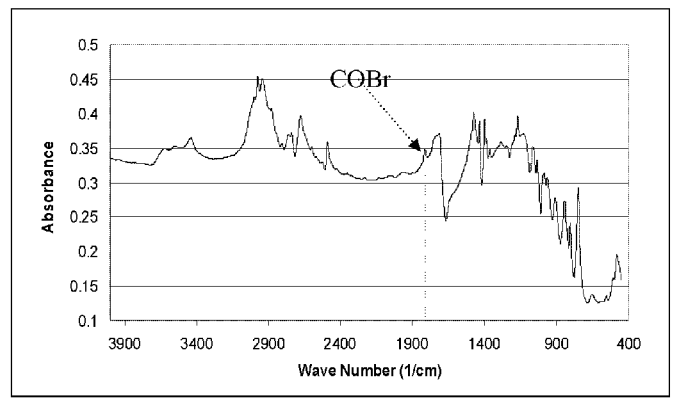
FIG. 9 is a graph of the FTIR profile of 2-bromopropionyl bromide modified PMMA beads according to an embodiment of the present invention.

FTIR analysis in a KBr disk was performed on the modified beads to confirm the surface modification. FIG. 9 shows the FTIR profile of 2-bromoisobutyryl bromide modified cross-linked PMMA beads, where the peak at 1813 $cm^{-1}$ is the COBr peak. Note the drop in the hydroxyl peak and the appearance of COBr at 1813 $cm^{-1}$ and 1168 $cm^{-1}$.

Atom Transfer Radical Polymerization (ATRP)

Atom transfer radical polymerization (ATRP) reaction was carried out in a Schlenk flask at room temperature for 24 hours in the presence of surface brominated PMMA beads, Cu(I) Br, Cu(II) Br, hydroquinone free MMA, and hexamethyl triethylene triamine. The product of the reaction was cleaned thoroughly, then weighed and imaged. Before the ATRP reaction, PMMA modified beads were 100 micron or less in diameter. Bead diameter increased after the reaction to as much as 200 microns. In addition, the weight of the beads was measured before and after the reaction. The weight increased by 200%.

Alternate Synthesis Route

Cross-linked PMMA nanospheres were synthesized as described in Example 10, infra, and were modified with ethanolamine and acryoyl chloride as previously described in Example 4, resulting in $CH_2=CH_2$ end groups on the surface of the PMMA beads that serve as initiation sites for graft polymerization of the PMMA brushes. Brush synthesis was carried out in a three-neck flask under a nitrogen atmosphere at 70° C. Potassium persulfate (KPS) was used as the initiator for free radical polymerization of MMA using water as the medium for suspension polymerization. Briefly, 1 g of acryloyl chloride modified nanospheres were dispersed in 80 mL of deionized water under vigorous stirring and the temperature was raised to 70° C. KPS was then added to the flask at a concentration ranging from 0.10-1.0 wt % and the mixture was stirred for 30 min. MMA monomer (5 to 15 wt %) was added dropwise to the medium and the reaction was carried out for 8 hrs. The product was collected and subjected to sohxlet extraction for 24 hr.

Example 7

Preparation of Bone Cement with PMMA-PMMA Spherical Brushes

This Example relates to the preparation of bone cement with PMMA-PMMA spherical brushes as synthesized in Example 6. The preparation of the third type of cement according to the present invention differs from the procedures for the first two types in that the polymer brushes will be the only solid polymer component added to the MMA, initiation chemicals, and radiopacifier in order to form the cement solutions (i.e., no linear polymer is dissolved).

One or more of the multi-solution bone cements according to the present invention have the capacity to meet the clinical need of improved cements for fixation of total joint replacements, along with other applications including vertebroplasty (VP) and kyphoplasty (KP) which are minimally invasive procedures used to treat vertebral compressive fractures. The change in form of cement, from powder-liquid to multi-solution based, significantly simplifies the mixing and delivery procedure in the operating room and produces a cement of more consistent quality, by eliminating variability in these processes. The multi-solution bone cements according to the present invention also have well controlled viscosities which remain relatively constant during the mixing and delivery process, as opposed to the viscosity of current commercial cements which is highly dynamic and increases significantly from the point of mixing to implantation of the cement. This property is particularly desirable for VP and KP applications.

Example 8

This example describes the effect of overall polymer-to-monomer ratio (P:M) and polymer bead (Pb) to linear polymer (Pl) ratio on the viscosity of modified multi solution bone cements.

Cross-linked polymer beads were synthesized. These beads consisted of 12% crosslinker with a nominal bead size of about 20 to 50 μm. These were made using suspension polymerization methods. Then, multi-solution bone cements were made with MMA monomer, 80,000 g/mol molecular weight linear PMMA polymer and the cross-linked PMMA beads. Various ratios of bead to linear polymer and total polymer to monomer were fabricated and their viscosity was determined using rheometric methods at room temperature. The ranges were: P:M ratio of 1.3:1 to 1.4:1, and Pb:Pl ratio of 1:1 to 2.5:1.

Figure 10:
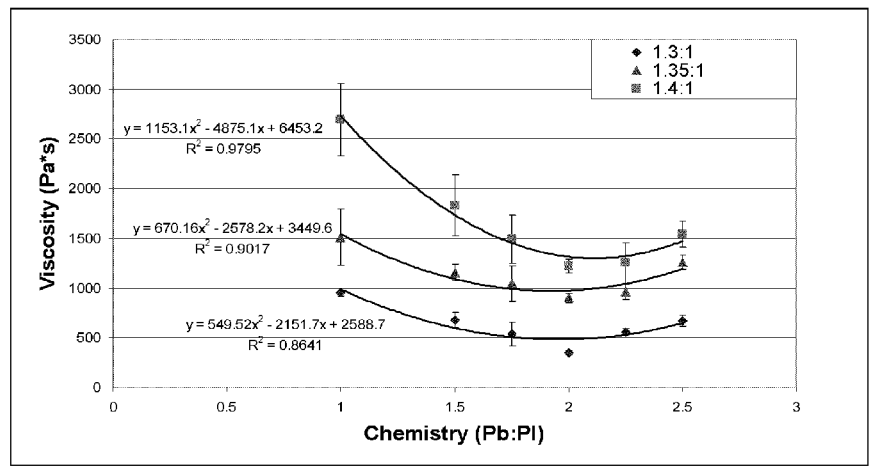
FIG. 10 is a graph of a summary of viscosity versus Pb:Pl ratio for three different P:M ratio multi-solution bone cements according to an embodiment of the present invention.

The results of viscosity testing are summarized in FIG. 10, which shows a summary of viscosity versus Pb:Pl ratio for three different P:M ratio multi solution bone cements. Note that the viscosity decreases with decreasing P:M ratio, and that increasing Pb:Pl ratio first decreases viscosity (below 2:1) and then slightly increases (above 2:1) viscosity.

It can be seen that the viscosity of the cement varies both with bead-to-linear-polymer ratio as well as polymer to monomer ratio. There is an increase in viscosity with increasing P:M ratio at every fixed Pb:Pl ratio. There is also a very interesting change in viscosity with ratio of bead polymer to linear polymer. There is a decrease, then slight increase in viscosity is the quantity of bead polymer is increased relative to linear polymer with a distinct minimum occurring at about 2:1 for all three P:M ratio cases. This indicates that the viscosity will decrease as the amount of bead polymer increases up to the 2:1 ratio. Above this ratio, increasing the Pb:Pl ratio slightly raises the viscosity and eventually the viscosity levels out (data not shown). These changes appear to reflect complex viscosity behavior where at less than the 2:1 ratio, the beads interfere with the mechanism of viscosity formation (primarily linear polymer chain sliding) and reduce the overall viscosity, whereas above 2:1, the viscosity increases as the bead-bead interactions begin to create increased viscosity.

This example shows that viscosity of multi-solution bone cement can be modified by the presence of cross-linked polymer beads, and that a minimum viscosity condition is developed at a ratio of Pb:Pl of around 2:1.

Example 9

This Example shows the mechanical properties of modified multi solution bone cement made from cross-linked polymer beads, linear polymer and monomer after the cements have been polymerized as they would be in-vivo.

Figure 11A:
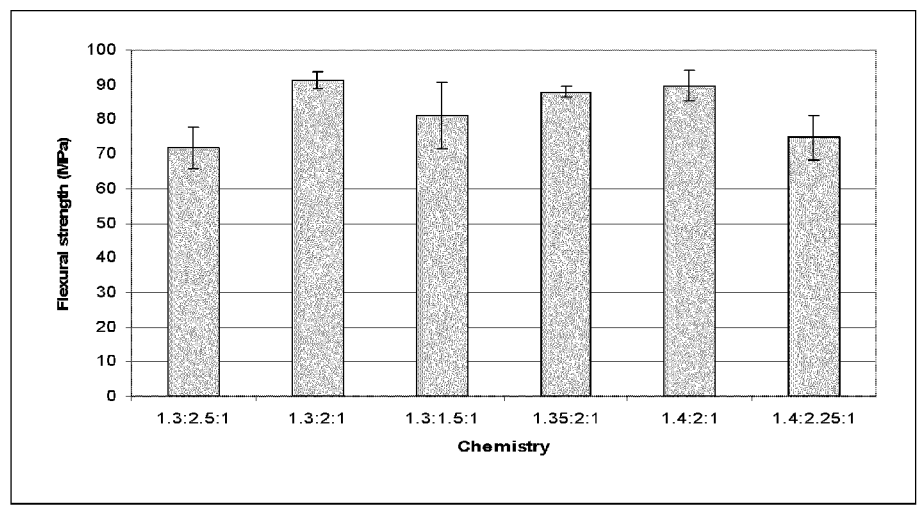
FIG. 11 shows the stress to failure, the strain to failure and the modulus of modified multi-solution bone cements according to an embodiment of the present invention.
Figure 11B:
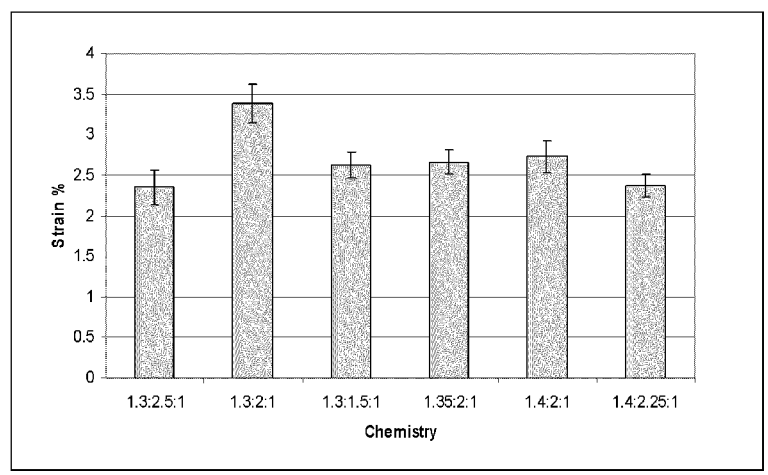
Figure 11C:
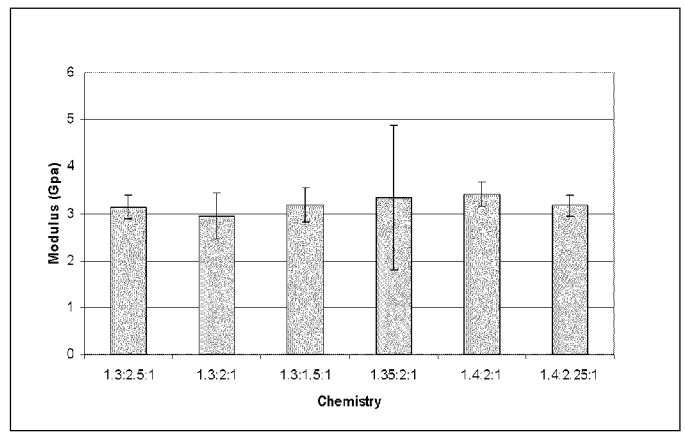

Modified multi solution bone cements consisting of linear 80,000 g/mol polymer, cross-linked polymer PMMA beads (with 12% EGDMA cross linker), MMA monomer and BPO and DMPT were used to make polymerized solid cement samples for mechanical testing. The Multi-solution mixtures were dispensed through a static mixing nozzle into rectangular Teflon molds approximately 3 mm×10 mm×40 mm. These samples were then used in three point bending flexural testing to determine the flexural strength (i.e., the stress to cause failure in 3-point bending), flexural modulus (E) and flexural strain to failure. The samples, once fabricated were measured and then tested on a mechanical test frame until failure. The stress, strain and modulus were determined using the standard equations for 3-point bending. The results are shown in FIG. 11 (11A-11C). Shown are the stress to failure, the strain to failure and the modulus. The x-axis nomenclature is such that the first number is the P:M ratio and the second set of numbers are the Pb:Pl ratio. For example, 1.3:2.5:1 means P:M ratio of 1.3:1 and Pb:Pl of 2.5:1. The results show that for a variety of combinations, the strength of the resulting polymerized cements ranges from 70 MPa to 90 MPa, the strain to failure ranges from 2.3 to 3.3 and the modulus is in the range of 3 GPa. All of these values are in the range of current commercial powder-liquid cements.

In an attempt to tailor viscosity and extend the application of this multi-solution bone cements, it has been shown herein that the viscosity of multi-solution cements can be manipulated by changes in the polymer-to-monomer ratio (denoted by P:M g PMMA/100 mL MMA) and by the addition of cross-linked particles (denoted by Pb) to the linear polymer (denoted by Pl) to make up the total polymer phase (e.g., the mixing of cross-linked microspheres or nanospheres (Pb) with the linear PMMA powder (Pl) at fixed ratios). Increasing the P:M ratio up to 1.4:1 significantly increased the viscosity of two-solution cements prepared with cross-linked PMMA microspheres, however increasing the Pb:Pl ratio at a fixed polymer-to-monomer composition had the effect of decreasing viscosity (up to a 2:1 ratio). These experiments confirmed the viability of tailoring viscosity without compromising the mechanical performance of two-solution cements for extended applications. Accordingly, the following Examples relate to the viscosity characteristics and curing parameters of novel multi-solution cements containing cross-linked PMMA microspheres (e.g., 20-100 μm) and nanospheres (e.g., 300-330 nm) added to the linear polymer phase, and are discussed for cements prepared at different compositions. The effect of PMMA particle size on these properties as well as the range of compositions suitable for applications in the treatment of vertebral compression fractures are also discussed.

Example 10

Exothermal Characteristics of Cements Containing Cross-linked Pmma Particles

This Example describes the effect of the addition of cross-linked microspheres and nanospheres on the exothermal behavior of two-solution cements, which was evaluated (at a fixed BPO:DMPT ratio of 1) and compared to the standard formulation of two-solution bone cements. The setting characteristics of standard two-solution bone cements have been previously characterized by Hasenwinkel and coworkers at specific BPO:DMPT molar ratios (see Hasenwinkel et al, *A novel high-viscosity, two-solution acrylic bone cement: effect of chemical composition on properties*, J. Biomed Mater Res 1999; 47:36-45; and Hasenwinkel et al, *Effect of initiation chemistry on the fracture toughness, fatigue strength, and residual monomer content of a novel high-viscosity, two-solution acrylic bone cement*, J Biomedical Materials Research 2002; 59, 411-421).

An additional variable in the modified two-solution cements of an embodiment of the present invention is the presence of two polymer phases: 1) dissolved linear PMMA ($P_L$) and 2) dispersed cross-linked PMMA microspheres or nanospheres ($P_b$). The linear PMMA (80,000 g/mol) was used as received (Dajac Laboratories, Feasterville Pa., USA) and the cross-linked beads were synthesized in house via two different polymerization techniques.

Briefly, PMMA microspheres were synthesized via suspension polymerization of methyl methacrylate (MMA), 7.5% v/v (Fluka) using water as the suspension medium, azobisisobutyro-nitrile (AIBN), 0.1% w/v (Sigma-Aldrich) as the initiator, polyvinyl alcohol (PVA), 2% w/v (Sigma-Aldrich) as the stabilizer and ethylene glycol dimethacrylate (EGDMA), 25% v/v (Aldrich) as the cross-linker agent. Microspheres were relatively polydisperse with diameter in the range 20-100 μm. PMMA nanospheres were synthesized via boiling temperature soap-free emulsion polymerization of MMA (6.25% v/v), using water as the dispersion medium, potassium persulfate (KPS), 0.1% w/v (Sigma-Aldrich) as the initiator and EGDMA (25% v/v) as the cross-linker. Resulting nanospheres were subjected to post-synthesis centrifugation for separation of supernatant and cleaning, followed by lyophilization for drying. This technique allows for the synthesis of monodisperse nanospheres ranging in size from 300 to 330 nm. For the preparation of two-solution cements, benzoyl peroxide (BPO) (Aldrich), N,N-dimethyl p-toluidine (DMPT) (Aldrich) and MMA (Fluka) (Aldrich) were used as received without further purification.

The preparation of the standard two-solution cement composed of linear PMMA followed the technique described by Hasenwinkel and coworkers, supra'. Cartridges of standard two-solution formulation were prepared at a P:M ratio of 0.9:1.

For the other modified two-solution cements, first the desired ratio of cross-linked nanospheres or microspheres ($P_b$) to linear PMMA ($P_l$) was determined. These two components were massed and mixed together forming the powder phase (P) of the subsequent mixture. Next, part of the total MMA volume was split and added to two graduated cylinders, in which one was mixed with 1.25 g of BPO (1.25 g/100 mL MMA) and the other with 0.7 mL DMPT (0.7 mL/100 mL). The two mixtures BPO/MMA and DMPT/MMA were transferred to two polypropylene cartridges followed by the addition of the powder phase. The remaining MMA volume added to the polypropylene cartridges. The polypropylene cartridges were sealed, vigorously agitated by hand and placed in a rotating drum mixer for 18 hours. Following mixing, the cartridges were stored upright at 4° C. The use of a radiopacifier was avoided in this Example in order to enhance the effect of the presence of a cross-linked phase and particle size on the behavior of novel two-solution cements. Additional Examples, set forth infra, will discuss the effects of elevated concentrations of a radiopacifier on the properties of the standard and modified two-solution bone cements.

The maximum polymerization temperatures and setting times of modified two-solution cements were measured, according to ASTM standard F451, and compared to the setting characteristics of standard two-solution cements. A smaller, custom-designed PTFE mold comprising a total volume of 3 mL was also used to record maximum polymerization temperatures and setting times of the cement compositions with the goal of replicating the approximate volume of cement delivered into a vertebral body during vertebroplasty. The maximum exotherm is defined as the peak in the temperature versus time curve during polymerization, while setting time is given by the time corresponding to the average temperature between ambient and maximum temperatures. Maximum temperatures and setting times are reported as the average of three measurements of each composition in both molds. Differences in maximum exotherm and setting times of compositions prepared with nanospheres and microspheres in comparison to the standard formulation were statistically analyzed using a Dunnett Test for multiple comparisons of all the cements with the control (STSBC) at a level of confidence of 95%. In order to evaluate the effect of particle size and polymer concentration in the groups of modified cements, linear contrasts between nanospheres and microspheres cements were performed. The setting parameters of cements were measured for the compositions described in Table 2, as follows:

TABLE 2

Cement compositions subjected to exothermal testing in the standard and custom designed molds.

| Cement formulation | P:M ratios | $P_b:P_l$ ratios |
|---|---|---|
| STSBC | Fixed 0.9:1 | — |
| Microspheres | 1:1, 1.1:1 | 1:1, 1.5:1, 2:1 |
| Nanospheres | 1:1, 1.1:1 | 1:1, 1.5:1, 2:1 |

These compositions were particularly selected based on suitable handling and flow rate of cements injected through a 12G and 15 cm needle attached to a mixing nozzle. Cements containing a large fraction of cross-linked particles ($P_b:P_l>2:1$) exhibited gritty appearance, which made injection more difficult due to clogging of material in the delivery needle.

Figure 12:
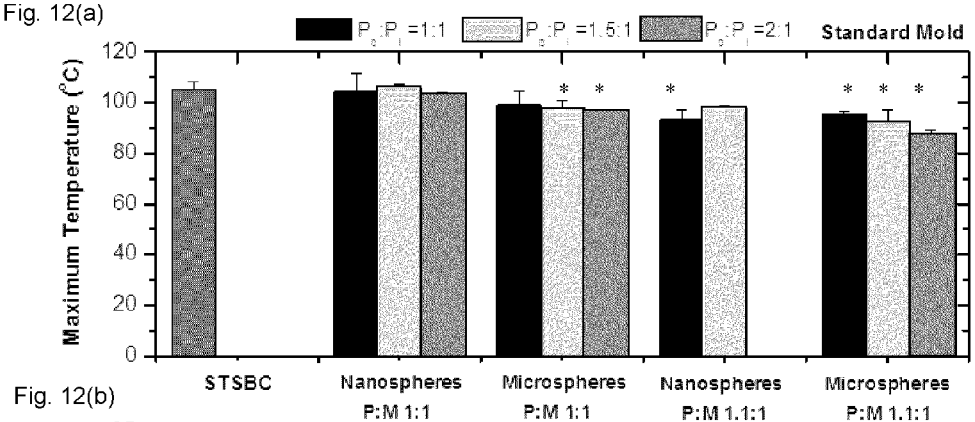
FIGS. 12a-b show the maximum polymerization temperatures and setting times, respectively, for cements containing cross-linked nanospheres and microspheres compared to STSBC, according to an embodiment of the present invention.
Figure 12:
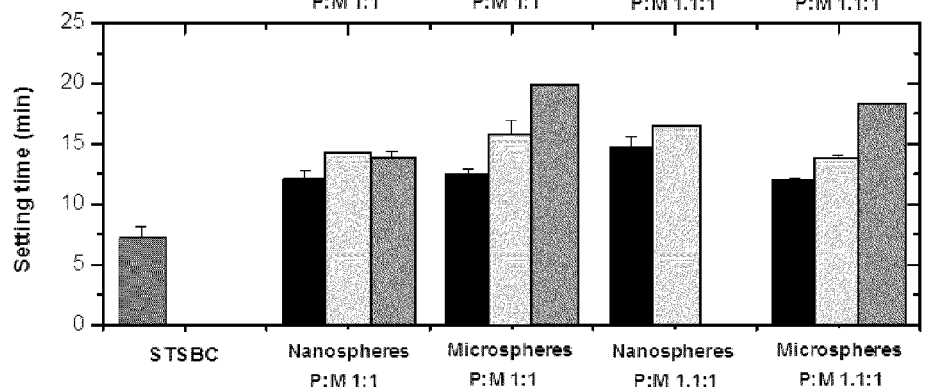
Figure 13:
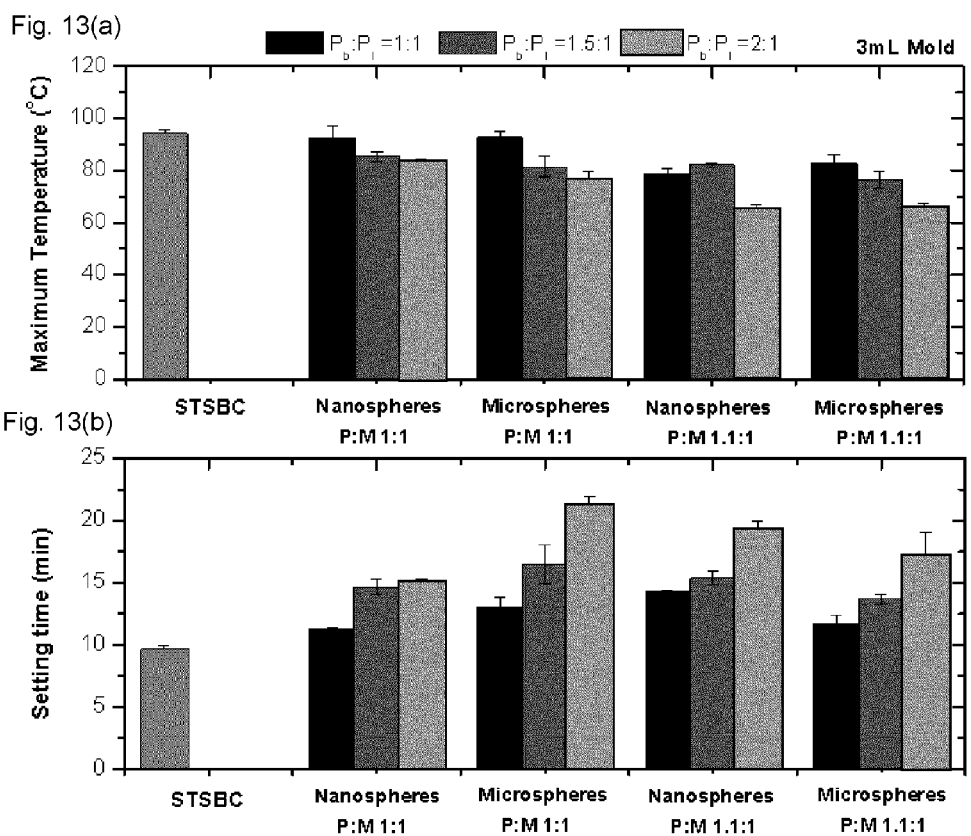
FIGS. 13a-b show the maximum polymerization temperatures and setting times, respectively, for cements containing cross-linked nanospheres and microspheres compared to STSBC, according to an embodiment of the present invention.

FIGS. 12-13 illustrate the exothermal characteristics of cements prepared with nanospheres and microspheres at P:M ratios of 1:1 and 1.1:1 as compared to STSBC (P:M ratio of 0.9:1) for experiments performed in the standard ASTM mold and a custom-designed mold with a 3 ml volume and XX mm thick, respectively.

FIGS. 12a and 12b show the maximum polymerization temperatures and setting times, respectively, for cements containing cross-linked nanospheres and microspheres compared to STSBC. Cements were prepared at increasing P:M and $P_b:P_l$ ratios. Results were obtained using a standard ASTM mold. The maximum polymerization temperature decreased and the setting time increased in comparison to the standard formulation across the cements compositions. The symbols (*) in the first panel (FIG. 12a) indicate the compositions which showed a significant difference compared to the control STSBC (p<0.05). In the second panel (FIG. 12b), all the composition showed a significant difference in comparison to the control STSBC (p<0.05).

In particular, FIG. 12a shows maximum polymerization temperatures of the different compositions being compared with the standard formulation (STSBC). The results show a significant (p<0.05) decrease in maximum exotherm for some of the compositions as indicated in the Figure. These compositions showed a decrease in maximum exotherm ranging from 8 to 18° C. compared to the STSBC. Additionally, there is a significant increase (p<0.05) in the setting time of cements (FIG. 12b) prepared with cross-linked microspheres and nanospheres for all of the compositions in comparison to the setting time of the standard formulation (approximately 7 minutes). Setting time increased at least 5.9 minutes (nanospheres-containing cements at a P:M of 1:1 with a $P_b:P_l$ of 1:1) and at most 12 minutes (microspheres-containing cement at a P:M of 1:1 with a $P_b:P_l$ of 2:1) with the addition of cross-linked particles.

FIGS. 13a and 13b show the maximum polymerization temperatures (FIG. 13a) and setting times (FIG. 13b) for cements containing cross-linked nanospheres and microspheres compared to STSBC. Cements were prepared at increasing P:M and $P_b:P_l$ ratios. Results were obtained using a custom-designed exothermal mold with a total volume of 3 mL. The results show that the maximum polymerization temperature decreased and the setting time increased in comparison to the standard formulation across the cements compositions. A significant decrease (p<0.05) in maximum temperatures for all the compositions in comparison to STSBC is shown, except nanospheres and microspheres-containing cements at a P:M of 1:1 with a $P_b:P_l$ of 1.5:1. The setting time of cements prepared with cross-linked particles increased significantly (p<0.05) in comparison to STSBC, except for nanospheres cement at a P:M of 1:1 with a $P_b:P_l$ of 1:1 and microspheres cement at a P:M of 1.1:1 with a $P_b:P_l$ of 1:1.

In particular, the exothermal parameters measured with the smaller mold in FIG. 13a showed a significant decrease (p<0.05) in maximum temperatures for all the compositions in comparison to the STSBC formulation, except in two cases (nanospheres and microspheres-containing cements at a P:M of 1:1 with a $P_b:P_l$ of 1.5:1). The reduction in maximum temperature with the addition of cross-linked particles ranged from 8.5 to 29° C. across compositions, in which nanospheres and microspheres containing cements prepared at a P:M of 1.1:1 with a $P_b:P_l$ of 2:1, presented the highest reduction in maximum polymerization temperature (27.6 and 29° C., respectively). Similar to the results illustrated in FIG. 12b, the setting time of cements prepared with cross-linked particles increased significantly (p<0.05) in comparison to the standard two-solution formulation (except for nanospheres cement at a P:M of 1:1 with a $P_b:P_l$ of 1:1 and microspheres cement at a P:M of 1.1:1 with a $P_b:P_l$ of 1:1, see FIG. 13b). The increase in setting time ranged from 3.5 minutes (microspheres-containing cements at a P:M of 1:1 with a $P_b:P_l$ of 1:1) to 11.5 minutes (microspheres-containing cements at a P:M of 1:1 with a $P_b:P_1$ 2:1) in comparison to the setting time measured for the standard formulation (approximately 9 minutes). Lower maximum polymerization temperatures were expected to be measured with the custom-designed mold due to the considerably smaller volume of material interacting with the thermocouple.

For all of the compositions tested, including those containing nanospheres and microspheres in the two molds, the results showed that when the content of cross-linked beads increased ($P_b:P_l$ ratio), the setting time became longer. The smaller volume of material polymerized in the 3 mL mold, in order to replicate the approximate amount delivered during surgery, exhibited lower exothermal temperatures but approximately the same setting time. The reduction in maximum temperature measured for cements containing a cross-linked phase may be associated with the dissipation of energy by the PMMA particles dispersed in the matrix. Nanospheres and microspheres may have had the role of an insulator, thereby absorbing and dissipating the excess of heat generated during curing of the cement.

Particle size does not have a strong effect on maximum temperature of two-solution cements containing cross-linked PMMA beads, showing significant differences between microspheres and nanospheres only when the groups are contrasted at a P:M of 1:1 (p<0.05) in both molds. When the contrast is performed at a P:M of 1.1:1 there is no significant difference between the groups of cements prepared with nanospheres and microspheres in both molds. On the contrary, there is a significant effect of particle size on the setting time of cements prepared with nanospheres and microspheres, in which the results showed significant differences when contrasted at both P:M ratios and in both molds. Microspheres-containing cements exhibited longer setting times at P:M of 1:1, while at P:M of 1.1:1 nanospheres cements had longer setting times.

Increasing the P:M ratio decreased the maximum exotherm of cements containing microspheres and nanospheres in the two different molds used in this study. Contrast analysis between nanospheres (or microspheres) cements prepared at P:M ratios of 1:1 and 1.1:1 revealed that there is a significant difference between the P:M ratios (p<0.05). Similarly there is a significant difference in setting time (p<0.05) among the compositions tested. Setting times of microspheres cement decrease with an increase in P:M, while nanospheres-containing cements exhibited an increase in setting time with increasing P:M. Studies of the effect of powder-to-liquid ratio (P:L) on the setting properties of commercial cements suggest that a reduction in setting time is expected with a increase in the P:L ratio. The addition of a cross-linked phase in the cement matrix resulted in lower exotherms and longer setting times for both cements containing cross-linked PMMA microspheres and nanospheres, without promoting increasing viscosity and deleterious effects on the mechanical properties of the material. In addition to the improved curing properties of the two-solution cements, the incorporation of a reinforcing cross-linked phase may also improve the mechanical properties of this material.

Example 11

Viscosity Behavior of Novel Two-solution Bone Cements

This Example describes the measurement of the static viscosities of the cements containing cross-linked PMMA beads of an embodiment of the present invention and the standard formulation. The static viscosity measurements were performed to evaluate the effect of the addition of cross-linked PMMA particles on the rheological behavior of two-solution cement formulations. Low viscosity coupled with a simultaneous decrease in the percentage of monomer is a desirable property in cements used for the treatment of vertebral compression fractures. Since the standard two-solution cement has a relatively high viscosity for a low polymer-to-monomer ratio, cross-linked spheres were added to the typical formulation in an attempt to lower viscosity and extend the application of the this material.

The static viscosities were measured using a digital viscometer (Brookfield viscometer DV-E) equipped with a coaxial spindle (SC4-14) and water-jacketed sample chamber (SC4-6R). The rheological measurements were performed at room temperature and at variable rotational speeds (from 1 to 100 rpm), depending on the range of viscosities of the different compositions, using the same spindle to perform all of the measurements. Shear rate is proportional to speed for a given spindle and for the combination of spindle/chamber used, taking into account geometry, this parameter was given by multiplying rotational speeds by a conversion factor 0.4. Prior to the start of the experiments, the instrument was calibrated using silicone oil calibration standards (Brookfield Engineering Laboratories Inc.) to ensure accurate readings within an error of +/-1% of any full scale spindle speed/viscosity range.

Cements were prepared, as described in the previous Example, and tested after a period of at least 3 days following mixing to allow complete swelling of the cross-linked particles in the cement solution. The compositions shown in Table 2, supra, were measured as well as the viscosity of microspheres-containing cements in a P:M range from 1:1 to 1.4:1 with $P_b:P_l$ from 1:1 to 4:1. However, at elevated concentrations of cross-linked particles a more powdery morphology resulted, making measurements of viscosity more complex due to quick wetting of the solutions. Therefore, these compositions are described more qualitatively in terms of suitability for use in KP and VP applications. Three measurements of each composition were performed at different shear rates and the average viscosity and standard deviation are reported herein.

Figure 14:
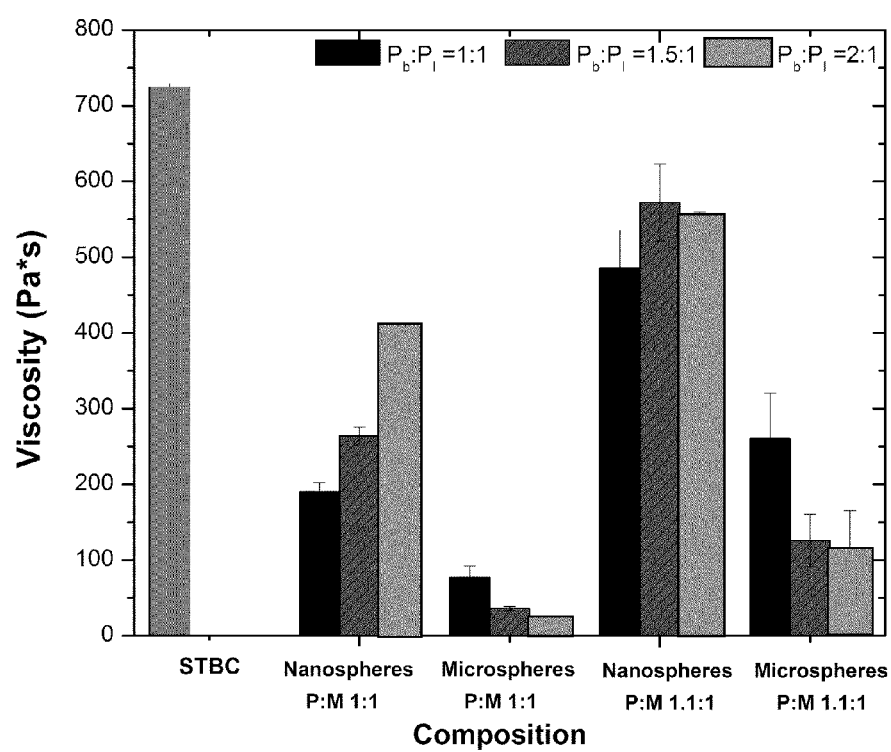
FIG. 14 shows the results of a comparison between viscosities of standard and modified-two solution bone cements at fixed shear rate ($4.8\ s^{-1}$), according to an embodiment of the present invention.

The results illustrated in FIG. 14 show a comparison between viscosities of standard and modified-two solution bone cements at fixed shear rate ($4.8 \, s^{-1}$). From this data it is evident that the addition of cross-linked PMMA nanospheres and microspheres significantly reduced viscosity (p<0.05) in comparison to the standard two-solution formulation. Cements composed of microspheres showed lower viscosities than cements prepared with nanospheres at the same P:M and $P_b:P_l$ ratios. The higher viscosity achieved with nanospheres-containing cements is a result of the increased surface area of the particles, and therefore improved diffusion of monomer into the smaller particles. This fact is confirmed by the higher swelling coefficients in MMA (Q) obtained for nanospheres in comparison to microspheres, 1.26 and 0.98 ml/g, respectively. Cements containing nanospheres and microspheres showed particular rheological behavior with the addition of increasing contents of cross-linked particles in the powder mixture ($P_b:P_l$ ratios).

Figure 15:
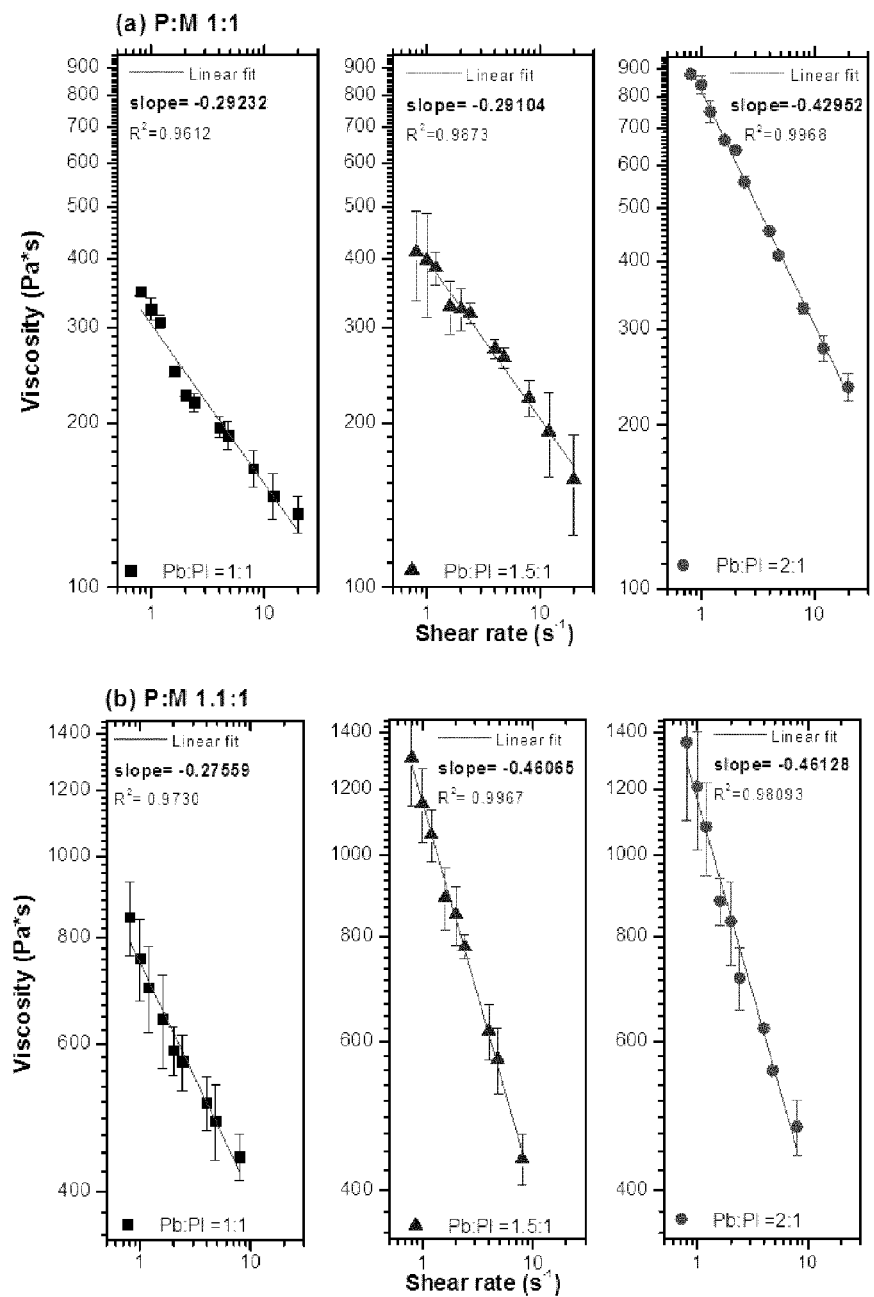
FIG. 15a-b show graphical plots illustrating viscosity as a function of increasing shear rate of nanospheres-containing cements (log-log scale), according to an embodiment of the present invention.
Figure 16:
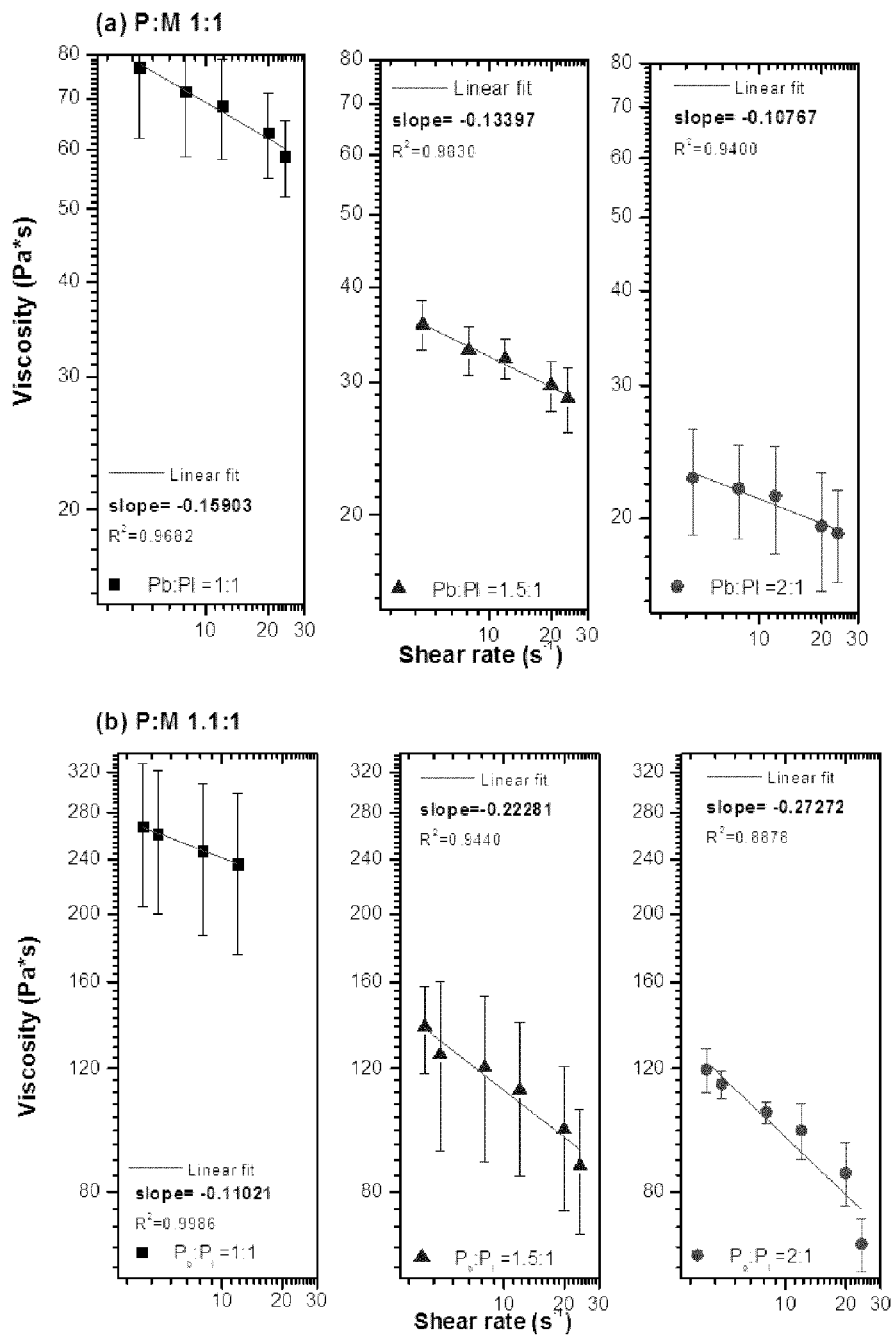
FIG. 16a-b show graphical plots illustrating viscosity as a function of increasing shear rate of nanospheres-containing cements (log-log scale), according to an embodiment of the present invention.

FIGS. 15-16 show graphical plots illustrating viscosity as a function of increasing shear rate of nanospheres-containing cements (log-log scale). The results in FIGS. 15 and 16 illustrate the range of viscosities measured at increasing shear rates for cements prepared with nanospheres and microspheres, respectively. The data is presented in double log plots for the different compositions compared (Table 2, supra). The slopes of the regression lines shown in FIGS. 15 and 16 give the type and degree of non-Newtonian flow, in which a slope zero would imply Newtonian behavior. Cements containing nanospheres exhibited an increase in viscosity with increasing volume fraction of particles in the mixture (highly non-Newtonian behavior), in which slopes varied from −0.29 to −0.43 with increasing $P_b:P_l$ for a P:M of 1:1 and from −0.27 to −0.46 for a P:M of 1.1:1. Cements containing microspheres showed the opposite behavior with respect to particle concentration, with decreasing viscosity at increasing $P_b:P_l$ ratio in the cement mixture. This cement also showed a lower degree of shear thinning with slopes varying from −0.16 to −0.10 with increasing $P_b:P_l$ ratio at a P:M of 1:1 and from −0.11 to −0.27 at a P:M of 1.1:1. STSBC was more pseudoplastic than microspheres-containing cements with a slope of −0.43 (data not shown).

Analyzing individual curves of viscosity versus shear rate, it was observed that the viscosity of microspheres-containing cements decreases only slightly with increasing shear over most of the shear rate range, while the viscosity of nanospheres containing-cements decreases almost linearly at higher shear rates (see FIG. 15, showing the linear decrease in viscosity with increasing shear rate at the two P:M ratios studied; FIG. 16 showing microspheres-containing cements presented a slight decrease in viscosity with increasing shear rate in which the slopes from the regression lines were lower than those measured for nanospheres-containing cements (as shown in FIG. 15)). This information is important to estimate the flow behavior of the different cements in restricted environments, such as in a small cannula or needle. Even though the viscosity of nanospheres-containing cement is higher, its more pseudoplastic nature explains the higher flow rate of this material in comparison to cements containing microspheres.

Figure 17:
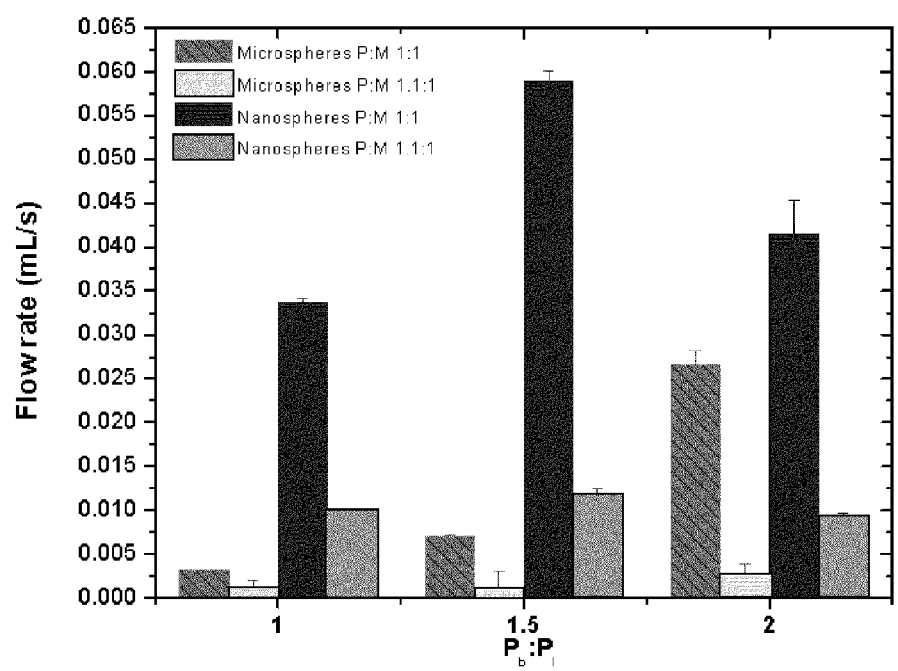
FIG. 17 shows the results of cements containing cross-linked nanospheres and microspheres prepared at different compositions, which were injected with a 12G and 15 cm long needle for evaluation of injectability, according to an embodiment of the present invention.

Cements prepared at different compositions were injected with a 12G and 15 cm long needle for evaluation of injectability, and the results are displayed in FIG. 17 (showing flow rate of cements containing nanospheres and microspheres at P:M ratios of 1:1 and 1.1:1). The results show that the flow rate is higher for nanospheres-containing cements, even though these compositions showed significantly higher viscosity than cements prepared with microspheres.

The observation of a weaker shear thinning behavior of microspheres-containing cements could explain the phenomenon of shear induced demixing observed with these materials. During injection of these cements separation of liquid monomer was visible during delivery. This separation led to clogging of microsphere particles in the delivery needle, which decreased flow rate significantly during injection. Even though the viscosity of nanospheres-containing cements is increased in comparison to microspheres, the injectability of these cements is suitable at a P:M of 1:1 and 1.1:1 at the $P_b$; $P_1$ ratios compared, as shown in FIG. 17. Above a $P_b$:$P_l$ ratio of 1.5:1 the mixture becomes very gritty and highly volatile, which made it difficult to measure viscosity due to the quick drying of the dough. At compositions above a P:M of 1.1:1 the increase in viscosity achieved with the addition of higher loads of nanospheres would not make this material suitable for delivery through small needles. Microspheres-containing cements, on the other hand, showed a decrease in viscosity with increasing volume fraction of particles. Viscosity decreased with an increase in $P_b$:$P_l$ at all P:M ratios explored, increasing with an increase in the P:M ratio. This decrease in viscosity, however, is apparent for $P_b$:$P_l$>2.5, since at these compositions the cements showed a very gritty and dry handling, which prevented continuing flow in the viscometer. Cement preparations above a P:M of 1.2:1 exceed the viscosity of the standard two-solution formulation. The range of viscosities suitable for injection is shown in FIG. 14.

The increase in viscosity achieved with the addition of a larger volume fraction of nanospheres in the cement solutions and the enhancement in non-Newtonian behavior observed for nanospheres-containing cements are consistent with previous results in the literature. The improved injectability of cements containing nanoparticles is a result of the more pronounced shear thinning achieved with the addition of smaller particles. The addition of cross-linked particles in the standard two-solution bone cement formulation was demonstrated to be an effective method to tailor viscosity making this material suitable for applications in the treatment of vertebral compression fractures.

The range of viscosities measured for cements modified with cross-linked PMMA microspheres and nanospheres combined with longer setting times must enable efficient delivery of material into the appropriate sites of fractured vertebral bodies, providing interdigitation with the cancellous bone. The addition of cross-linked nanospheres and microspheres in Examples 10 and 11 were shown to reduce the maximum exotherm when higher volume fractions of particles are employed and to significantly increase the setting time. Likewise, viscosity was significantly reduced in comparison to the standard formulation at higher polymer-to-monomer ratios. Taking into account that the standard two-solution bone cement has been shown to exhibit superior properties and easy preparation and handling, the modification of these cements thorough the addition of cross-linked particles was demonstrated to successfully tailor the viscosity and exothermal properties of this material, making it more suitable for applications in the treatment of compression fractures.

As detailed in some of the previous Examples, the viscosity of two-solution cements can be manipulated by subtle changes in the polymer-to-monomer ratio (denoted by P:M, g PMMA/100 mL MMA) and by the addition of cross-linked beads in the linear polymer phase. This additional variable involves mixing of cross-linked microspheres or nanospheres (denoted by $P_b$) with the linear PMMA powder (denoted by $P_l$) at fixed ratios. It was discussed that increasing the P:M ratio up to 1.4:1 significantly increased the viscosity of two-solution cements prepared with cross-linked PMMA microspheres, however increasing the $P_b$:$P_l$ ratio at a fixed polymer-to-monomer composition had the effect of decreasing viscosity (up to a 2:1 ratio). This disclosure confirmed the viability of tailoring viscosity without compromising the mechanical performance of two-solution cements for extended applications.

In the following Examples, the effects of the addition of $ZrO_2$, in concentrations tuned for fluoroscopic visualization, on the material properties of novel two-solution bone cements modified by the addition of cross-linked PMMA nanospheres or microspheres in the powder phase are described. The influence of increasing radiopacifier concentration on the compressive strength, porosity, viscosity and curing parameters of these cements is also discussed.

Example 12

Cement Formulations and Powder Morphology

This Example describes the synthesis of PMMA microspheres and PMMA nanospheres. An additional variable in the modified two-solution cements of an embodiment of the present invention is the presence of two polymer phases: 1) dissolved linear PMMA ($P_l$) and 2) dispersed cross-linked PMMA microspheres or nanospheres ($P_b$). The linear PMMA (80,000 g/mol) was used as received (Dajac Laboratories, Feasterville Pa., USA) and the cross-linked beads were synthesized via two different polymerization techniques.

Briefly, PMMA microspheres were synthesized via suspension polymerization of methyl methacrylate (MMA), 7.5% v/v (Fluka) using water as the suspension medium, azobisisobutyro-nitrile (AIBN), 0.1% w/v (Sigma-Aldrich) as the initiator, poly-vinyl alcohol (PVA), 2% w/v (Sigma-Aldrich) as the stabilizer and ethylene glycol dimethacrylate (EGDMA), 25% v/v (Aldrich) as the cross-linker agent. Microspheres presented a relatively high polydispersity with diameters in the range 20-100 µm.

PMMA nanospheres were synthesized via boiling temperature soap-free emulsion polymerization of MMA (6.25% v/v), using water as the dispersion medium, potassium persulfate (KPS), 0.1% w/v (Sigma-Aldrich) as the initiator and EGDMA (25% v/v) as the cross-linker. Resulting nanospheres were subjected to post-synthesis centrifugation for separation of supernatant and cleaning, followed by lyophilization for drying. This technique allows for the synthesis of monodisperse nanospheres ranging in size from 300 to 330 nm. For the preparation of two-solution cements, benzoyl peroxide (BPO) (Aldrich), N,N-dimethyl p-toluidine (DMPT) (Aldrich), MMA (Fluka) and $ZrO_2$ (Aldrich) were used as received without further purification. KyphX HV-R (Kyphon Inc, Sunnyvale, Calif.) containing 30% $BaSO_4$ was used as the control for the compression experiments and optical density measurements. This cement has been broadly used clinically in the treatment of vertebral compression fractures due to its low initial viscosity and extended dough time as compared to other commercial cements.

Example 13

Standard Cements Preparation

This Example describes the preparation of the standard two-solution cement composed of linear PMMA has been described by Hasenwinkel and coworkers (see Hasenwinkel et al, *A novel high-viscosity, two-solution acrylic bone* cement: *effect of chemical composition on properties*, J. Biomed Mater Res 1999; 47:36-45; and Hasenwinkel et al, *Effect of initiation chemistry on the fracture toughness, fatigue strength, and residual monomer content of a novel high-viscosity, two-solution acrylic bone cement*, J Biomedical Materials Research 2002; 59, 411-421), and the preparation of modified two-solution cements of an embodiment of the present invention.

Briefly, cartridges of standard two-solution formulation were prepared at a 0.9:1 P:M ratio.

For the modified two-solution cement compositions, first the desired ratio of cross-linked nanospheres or microspheres ($P_b$) to linear PMMA ($P_l$) was determined. These two components were massed and mixed together forming the powder phase (P) of the subsequent mixture. A fixed 1:1 P:M ratio with 1.5:1 $P_b$:$P_l$ was used throughout the course of the experiments and this composition was specifically selected based on handling and injectability properties. Next, part of the total MMA volume was split and added to two graduated cylinders, in which one was mixed with 1.25 g of BPO (1.25 g/100 mL MMA) and the other with 0.7 mL DMPT (0.7 mL/100 mL). The two mixtures BPO/MMA and DMPT/MMA were transferred to two polypropylene cartridges followed by the addition of the powder phase. The remaining MMA volume was mixed with zirconium dioxide ($ZrO_2$) in concentrations of 5, 20 and 30% (w/v), vigorously agitated and transferred to the polypropylene cartridges. Radiolucent cements were also made for comparison. The polypropylene cartridges were sealed, vigorously agitated by hand and placed in a rotating drum mixer for 18 hours. Following mixing, the cartridges were stored upright at 4° C. Upon demand, the solutions can be mixed through a static mixing nozzle. KyphX was prepared according to manufacturer instructions.

Example 14

Preparation of Samples for Mechanical Testing and Optical Density Measurements

This Example describes the preparation of the standard two-solution cement composition, and the modified two-solution cement compositions (as described in the previous Example), with $ZrO_2$. Cements of all three compositions were prepared at 0, 5, 20 and 30% $ZrO_2$ and injected into a Teflon mold consisting of cylindrical holes, each 6 mm in diameter and 12 mm height, for the casting of compression samples as per ASTM standard F451-99a. The cylindrical samples were allowed to polymerize in the mold for 1 hour followed by 24 hours of curing in air after removal from the mold. The specimens were sanded flush with 400-grit sand paper and were visually inspected for defects. Samples presenting external voids or defects greater than 0.5 mm were excluded. Three samples from each composition were randomly selected from the pool of samples and imaged with X-ray for evaluation of optical density. Measurements of sample height and diameter were taken with a digital micrometer.

Example 15

Optical Density Measurements and Porosity Evaluation

This Example describes optical density measurements of the standard two-solution cement composition, and the modified two-solution cement compositions with $ZrO_2$ (as described in the previous Example).

Optical density measurements were obtained from the digital x-ray images. These images were taken in air at an x-ray tube voltage of 42 kV. This voltage can give excellent information about details (small pores, fractures) in small bone cement specimens when they are studied surrounded by air.

The contrast in an image on an electronic display or monitor is in the form of different brightness or brightness ratios between various points within the image area. Radiopacity (or contrast) is determined by comparing the images of the test specimen and its background on the x-ray film or digital image. The optical density values vary from 0 to 255. Kjellson et al defined contrast as a local difference (ΔI) in the transmitted x-ray intensity through a subject compared with the transmitted x-ray intensity through the adjacent background as:

$$\text{Contrast} = \frac{I_{max} - I_{min}}{I_{max}} \quad (1)$$

Where, $I_{max}$ represents transmittance through the background (or brightness) and $I_{min}$ the transmittance of the subject (see Kjellson F, Almen T, Tanner K E, McCarthy I D, Lidgren, *Bone cement X-ray contrast media: A clinically relevant method of measuring their efficiency*, J Biomed Mater Res B: Appl Biomater 2004; 70B:354-361).

Photoshop (Adobe Version 8.0) was used to measure the gray scale (brightness index) of the specimens and of the immediately adjacent background. A line was drawn parallel to the sample vertical axis and 15 measurements of brightness were taken randomly along this line paired with the immediately adjacent background for each group of samples (5 random measurements in each specimen). The contrast was determined using equation (1) and average contrast and standard deviations were calculated for each group of samples. Differences in contrast with increasing concentration of radiopacifier for groups of cements prepared with nanospheres, microspheres, and STSBC were statistically evaluated using two-way ANOVA with simple effect analysis at a level of significance of 95%.

The distribution of pores within the samples was qualitatively characterized using scanning electron microscopy (SEM-JEOL 5600) in both secondary and backscattered electron imaging. Prior to imaging, the samples were cross-sectioned and gently polished with running water and sand paper grits-600 and 1200, and the polishing was completed with an alumina solution (0.05 µm) until obtaining a mirror-like surface free of scratches. The polished surface was gold sputtered for 80 seconds and SEM micrographs were taken with voltages in the range 10-13 kV.

Figure 18:
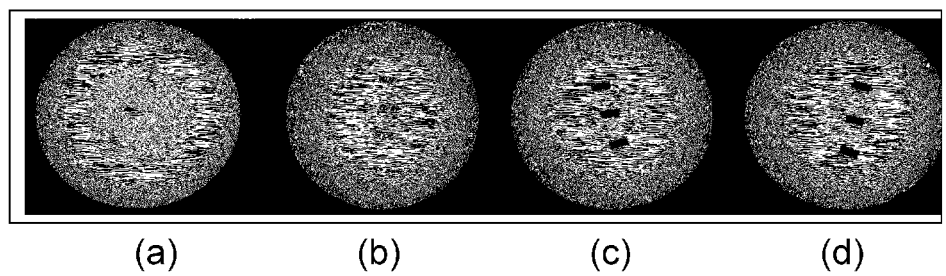
FIG. 18 shows x-ray images of modified two-solution cements prepared with nanospheres at (a) 0% $ZrO_2$ (b) 5% $ZrO_2$ (c) 20% $ZrO_2$ and (d) 30% $ZrO_2$, according to an embodiment of the present invention.

The results show that optical density increased linearly as a function of radiopacifier concentration in the three two-solution formulations evaluated. Radiographs of the various cement preparations were obtained as illustrated in FIG. 18, and the optical densities of all compositions are compared in FIG. 19. Specimens without $ZrO_2$ were not completely transparent to x-rays.

FIG. 18 shows x-ray images of modified two-solution cement prepared with nanospheres at (a) 0% $ZrO_2$ (b) 5% $ZrO_2$ (c) 20% $ZrO_2$ and (d) 30% $ZrO_2$. There is an increase in contrast with increasing concentration of radiopacifier up to 30%. The cement prepared at 0% $ZrO_2$ was not completely transparent to x-rays.

Figure 19:
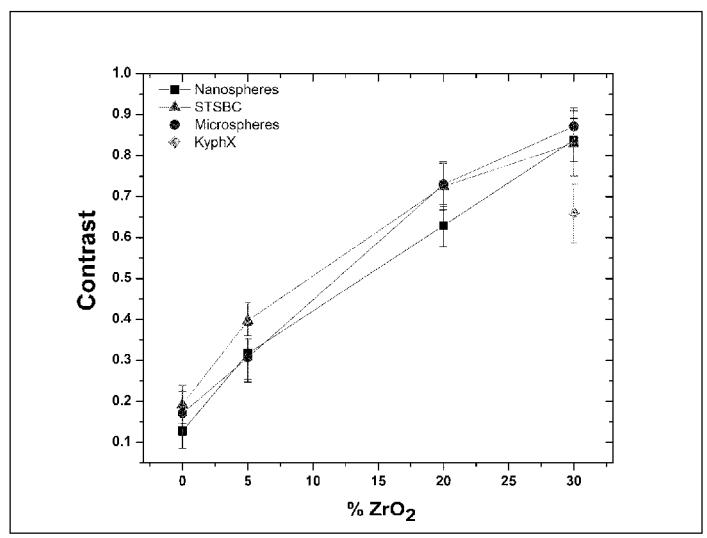
FIG. 19 shows the contrast values comparison for two-solution cement preparations (standard and modified with microspheres and nanospheres) with increasing radiopacifier concentrations, according to an embodiment of the present invention.

FIG. 19 shows the contrast values comparison for two-solution cement preparations (standard and modified with microspheres and nanospheres) with increasing radiopacifier concentrations. X-ray images of cylindrical bone cement samples were taken in air at an x-ray tube voltage of 42 kV.

KyphX (♦) presented lower optical density than the three cement formulations prepared at 30% $ZrO_2$, presenting contrast values in the range of two-solution cements containing 20% $ZrO_2$. The data shows a significant increase in radiopacity with increasing concentration of $ZrO_2$ for STSBC (▲), nanospheres (■) and microsheres (●) cements (p<0.05).

As shown in FIG. 19, the contrast values between the area corresponding to the specimen and the background increased with increasing $ZrO_2$ content across the three formulations. The standard deviations are somewhat high, probably due to the presence of internal porosity and inhomogeneity of the cement matrices. The standard deviations are particularly high for KyphX and standard two-solution compositions. There is a significant increase in contrast with increasing concentration of $ZrO_2$ in all the three cement formulations (p<0.05). Also, there is a significant difference in contrast (p<0.05) among the three cement compositions compared at 0% (except between STSBC and microspheres), 5% (except between nanospheres and microspheres) and 20% (except between microspheres and STSBC). At 30% $ZrO_2$ the contrast values of cements containing nanospheres, microspheres or the standard formulation are not significantly different (p>0.05). KyphX (30% $BaSO_4$) has contrast in the range found for 20% $ZrO_2$ with the three different cements and has lower contrast than the cements prepared at 30% $ZrO_2$.

These results are in agreement with the contrast values measured by Kjellson et al for acrylic bone cements specimens containing 5% (contrast value 0.339) and 15% (contrast value 0.733) $ZrO_2$ imaged under the same x-ray tube voltage (40 kV) and conditions applied as described herein (see Kjellson F, Almen T, Tanner K E, McCarthy I D, Lidgren, *Bone cement X-ray contrast media: A clinically relevant method of measuring their efficiency*, J Biomed Mater Res B: Appl Biomater 2004; 70B:354-361). Indeed cements containing $ZrO_2$ are expected to have higher opacity than those containing $BaSO_4$ when imaged at an accelerating voltage of 40 kV because this voltage produces its peak intensity just above the zirconium K-border (18 kV). These results point out the possibility of reducing the concentration of radiopacifier below 30% when $ZrO_2$ is used instead of $BaSO_4$. This last observation is important considering that viscosity was observed to increase with the addition of increasing concentrations of radiopacifier.

Example 16

Compression Testing

This Example describes compression testing of the standard and modified bone cement compositions, as described in the previous Examples. Standard and modified two-solution bone cements and the control KyphX were subjected to compression testing in an MTS hydraulic system (model #) with a 22.5 kN capacity load cell. The cylindrical samples were tested at room temperature at a displacement rate of 0.05 mm/s. The specimens were placed individually between two steel parallel platens and compressed to 50% strain. Five samples of each composition were tested in compression. Stress and strain data were obtained by dividing the load and deformation by the cross-sectional area and initial length of the specimens, respectively. Ultimate compressive stress was defined as the peak stress while compressive yield strength was determined using the 2% offset method of the Hookean portion. Compressive modulus was calculated from the slope of the linear region of the stress-strain curve. Two-way ANOVA with simple effects analysis was applied at a level of significance of 95% to determine the effect of cement composition and radiopacifier concentration on each variable measured in the compression test (ultimate compressive stress, modulus and strain to failure).

Porosity

Porosity was qualitatively evaluated in cylindrical samples casted for compression testing, as described above. The different cement preparations presented particular porosity distribution as shown in FIG. 20.

Figure 20:
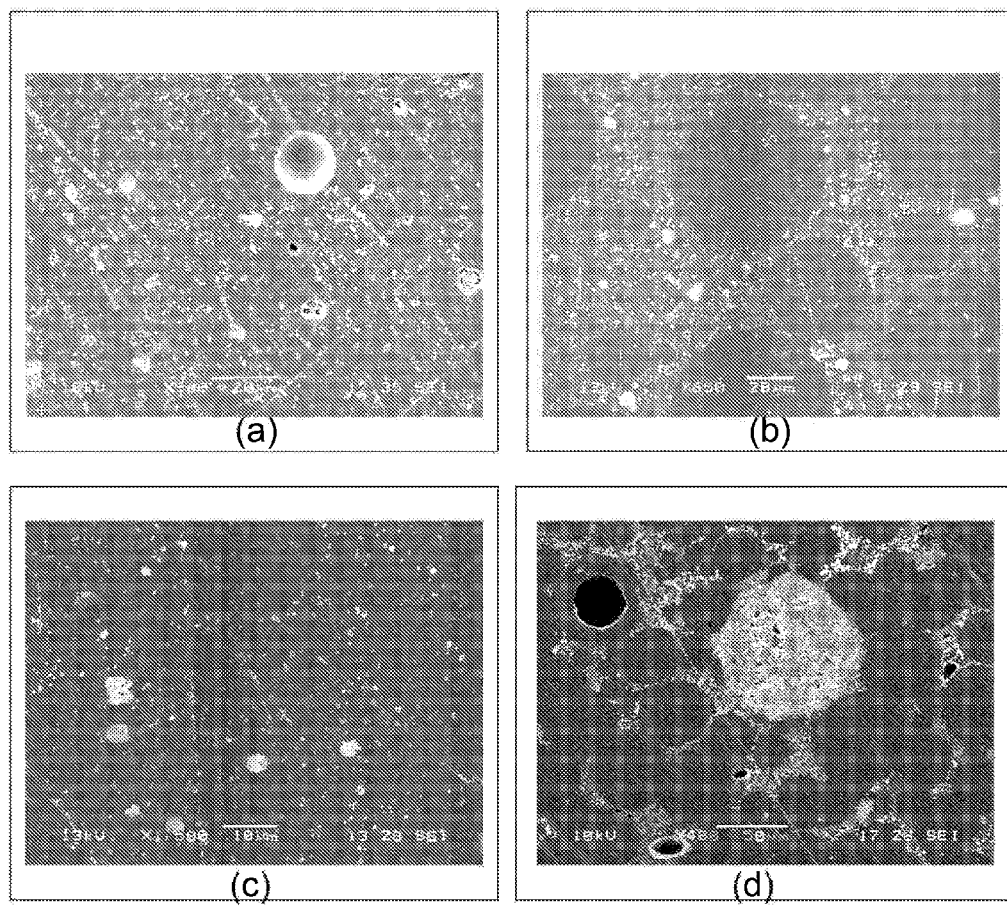
FIG. 20 shows secondary electron SEM images illustrating porosity distribution of the standard and modified bone cement compositions (mid-section of cylindrical specimens prepared at 30% $ZrO_2$), according to an embodiment of the present invention.

FIG. 20 shows secondary electron SEM images illustrating porosity distribution of the standard and modified bone cement compositions (mid-section of cylindrical specimens prepared at 30% $ZrO_2$). FIG. 20 shows (a) STSBC (900X) (b) microspheres-containing cements (650X) (c) nanospheres-containing cements (1500X), and (d) KyphX (400X) at 30% $BaSO_4$. There is a presence of micropores in the standard two-solution and KyphX formulations. White agglomerations are evidence of radiopacifier clumps, which are larger for the KyphX formulation.

As shown in FIG. 20, clumps of radiopacifier can be clearly identified as white agglomerates on the surface. A visual inspection of the cross-sections of the samples revealed that the incidence of macropores (defined as pores with diameter ≥1 mm) was more frequent in cement preparations with the standard two-solution formulation (a) and KyphX (d). The KyphX formulation showed the typical $BaSO_4$ agglomeration discussed in the literature, with large clumps (about 50 μm in diameter) present all over the surface cross-sections. PMMA beads were also observed surrounded by regions of polymer matrix containing a great extent of microporosity (defined as pores with diameter <1 mm). Microspheres-containing cements showed pores formed by the removal of polymer beads from the cement matrix (about 100 μm in diameter). Conversely, nanospheres-containing cements presented very few macropores distributed on the outer interfaces of the samples, and only very small micropores were visible on the cross-sections. Qualitatively there was an evident difference in the appearance of the matrices containing $ZrO_2$ and $BaSO_4$. The larger extent of pores in the KyphX cement might translate into lower strengths and nucleation sites for crack propagation. Kurtz et al observed that three different bone cements presented porosity in which $BaSO_4$ was observed as an agglomerate of particles with typical length scales on the order of 1 μm (see Kurtz S M, Villarraga M L, Zhao K, Edidin A A, *Static and fatigue mechanical behavior of bone cement with elevated barium sulffate content for treatment of vertebral compression fractures*, Biomaterials 2005; 26:3699-3712). In this paper, Kurtz et al found no correlation between the $BaSO_4$ content and the incidence of macroporosity, suggesting that other factors, mainly the composition of the cement matrix, may influence the generation of large pores.

It is important to point out that $ZrO_2$ was added to two-solution cements instead of $BaSO_4$ due to a detrimental effect observed when mixing this contrast agent into solutions containing nanospheres. $BaSO_4$ led to the formation of a powdery mixture of difficult handling, which could not be mixed or delivered through a static nozzle. It could be argued that the increased surface area of the particles exposed to the monomer solution (nanospheres plus $BaSO_4$ particles, which have size distribution in the nano-scale range) induced this effect due to more difficult wetting. However, even at very low concentrations of $BaSO_4$ (2 and 5%) the same detrimental effect was observed. This observation indicates that $BaSO_4$ may be inappropriate for the modified two-solution cements, described herein. This negative effect was not observed when $ZrO_2$ was added to the solutions, on the contrary the cements presented suitable handling allowing the casting of samples with only a few signs of external porosity or clumping of radiopacifier.

Example 17

Compression Testing and Fracture Analysis

This Example discusses the results of compression tests that were performed to investigate the effect of the addition of increasing concentrations of $ZrO_2$ on the mechanical behavior of two-solution cement preparations. The results show that the static compressive strength of cements containing cross-linked beads exceeded the 70 MPa minimum specification (ASTM F451-99a, as should be understood by those of ordinary skill of the art) for all the compositions investigated, except STSBC containing increasing content of $ZrO_2$.

Figure 21:
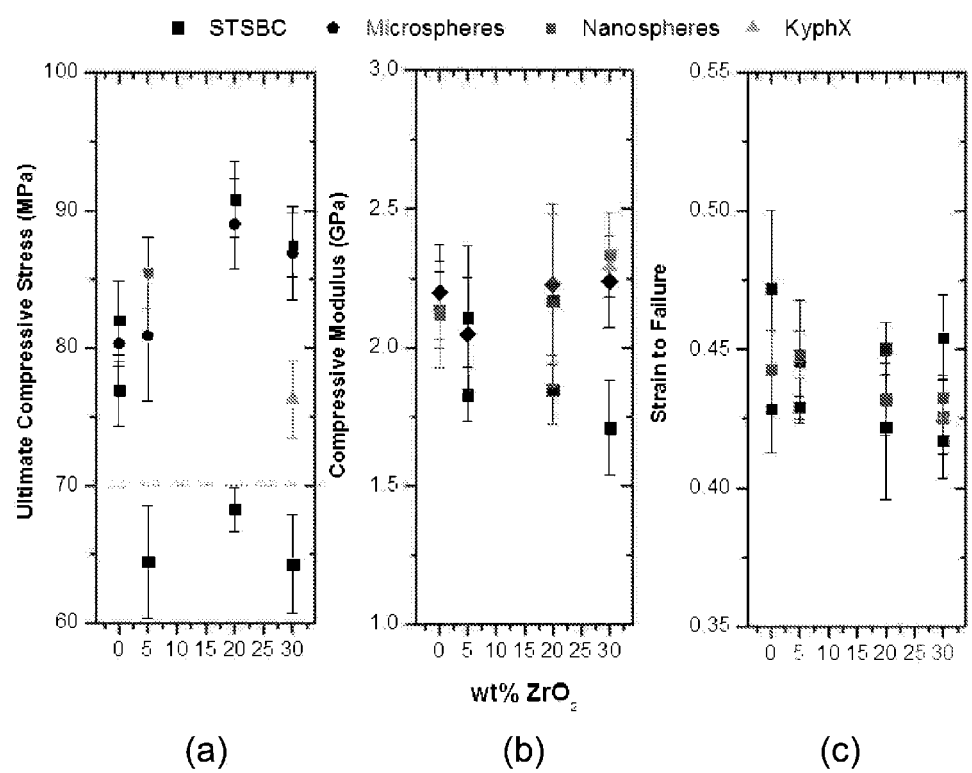
FIG. 21 shows an overall comparison between the compressive properties (compression strength, modulus and strain to failure) of modified cements containing microspheres and nanospheres, and the standard formulation prepared with increasing concentrations of $ZrO_2$, according to an embodiment of the present invention.

FIG. 21 shows an overall comparison between the compressive properties (compression strength, modulus and strain to failure) of modified cements containing microspheres and nanospheres, and the standard formulation prepared with increasing concentrations of $ZrO_2$. A comparison was also made to KyphX at 30% radiopacifier. Compressive yield strength presented values close to the ultimate compressive stress, therefore the data was omitted. FIG. 21 shows ultimate compressive stress (a), compressive modulus (b) and strain to failure (c). Cements prepared with cross-linked particles show significantly higher compressive strength than STSBC ($p<0.05$). The compressive strength of the KyphX cement is lower than the strengths of the modified two solution cements but higher than STSBC.

Microspheres and nanospheres containing cements presented surprisingly high compressive strength, as shown in FIG. 21 (a). This parameter increased significantly with an increase in radiopacifier concentration up to 30% for both formulations ($p<0.05$), reaching compressive strength values higher than 90 MPa (nanospheres-containing cement at 20% $ZrO_2$). In contrast, the standard two-solution formulation showed a significant decrease in compressive strength with an increase in $ZrO_2$ content ($p<0.05$). Simple effects analysis indicated that the mean compressive strength of nanospheres and microspheres-containing cements are not significantly different ($p>0.05$) (the only significant difference in strength was found at 5% $ZrO_2$); however there is a significant difference between the strengths of these two cements and that of the standard two-solution formulation ($p<0.05$) compared at 0, 5, 20 and 30% $ZrO_2$. KyphX showed compressive strength values between the standard two-solution formulation and cements containing cross-linked particles (average approximately 75 MPa). The behavior of the compressive modulus for the three cement formulations and KyphX is illustrated in FIG. 21(b). There was no significant effect of increasing $ZrO_2$ concentrations on the moduli of cements containing nanospheres and microspheres ($p>0.05$), however STSBC showed a significant decrease in modulus with increasing concentration of radiopacifier in the material ($p<0.05$). Similarly to compressive strength, simple effects analysis indicated that the compressive modulus of nanospheres and microspheres-containing cements are not significantly different ($p>0.05$); however there is a significant difference between the moduli of nanospheres and microspheres-containing cements compared to those of the standard two-solution formulation ($p<0.05$) at 20 and 30% $ZrO_2$. Strain to failure is shown in FIG. 21(c) for the three cement formulations and KyphX. This parameter shows a significant difference across $ZrO_2$ compositions for microspheres-containing cements and STSBC ($p<0.05$). Contrary, there is no significant effect of $ZrO_2$ concentration on the strain to failure of cements prepared with nanospheres. Simple effects analysis of this parameter also indicated that the strain to failure of nanospheres and microspheres-containing cements are not significantly different; however there is a significant difference between the strains of these two cements and those measured for the standard two-solution formulation ($p<0.05$) (microspheres and STSBC at 0, 20 and 30% $ZrO_2$ and nanospheres and STSBC at 0 and 30%).

The ultimate compressive strength of STSBC cement containing 5, 20 and 30% $ZrO_2$ is below the 70 MPa minimum ASTM requirement. These results indicate that STSBC would not be suitable for the treatment of vertebral compression fractures. The addition of $ZrO_2$ even at a very low concentration (5%) had deleterious effects on the compressive strength of the material. At 30% radiopacifier the results reveal that cements prepared with nanospheres and microspheres have higher compressive strength than KyphX. There is no effect of the PMMA particle size on the compressive properties of two solution-cements containing increasing concentrations of $ZrO_2$, considering the statistical analysis did not indicate any significant differences between microspheres and nanospheres-containing cements in the three parameters evaluated.

The compressive properties measured for modified two-solution cements confirmed that these materials are appropriate to withstand the high loads exerted in the spine and can be designed with sufficiently high levels of $ZrO_2$ to permit visualization under fluoroscopy. Materials properties reported were obtained from compression testing, which is the predominant mode of loading in the spine in vivo. The values reported are higher or in the range of results previously obtained in the literature. For example, Jasper et al measured compressive properties of several conventional commercial cements used in vertebroplasty obtaining compressive modulus ranging from 2.0-2.7 GPa and compressive yield strength and ultimate compressive strength ranging from 50-73 MPa and from 53-80 MPa, respectively (see Jasper L E, Deramond H, Mathis J M, Belkoff S M, *Material properties of various cements for use with vertebroplasty*, J Mater Sci: Mater Med 2002; 13:1-5). $ZrO_2$ in increasing concentrations in modified two-solution cements acted as a rigid reinforcing phase when interacting with the cross-linked beads in the cement matrix. The radiopacifier in this case may have promoted an interaction between the crack fronts and the second phase dispersion, blunting further crack propagation. In contrast, the addition of $ZrO_2$ in standard two-solution cement did not reinforce the matrix, even though a fair distribution of the radiopacifier was observed, as illustrated in FIG. 20(a). Some of the possible reasons for this result are higher porosity associated with the standard formulation and therefore presence of more sites for crack nucleation, higher viscosity of the dough which does not allow for air bubbles to escape during mixing, and lack of the first phase dispersion (cross-linked particles) which is thought to provide a barrier to crack propagation. The combination of cross-linked beads with the second phase dispersion (considering $ZrO_2$ did not produce significant clumping in the material) allowed for improved mechanical anchorage in the cement matrix.

Figure 22:
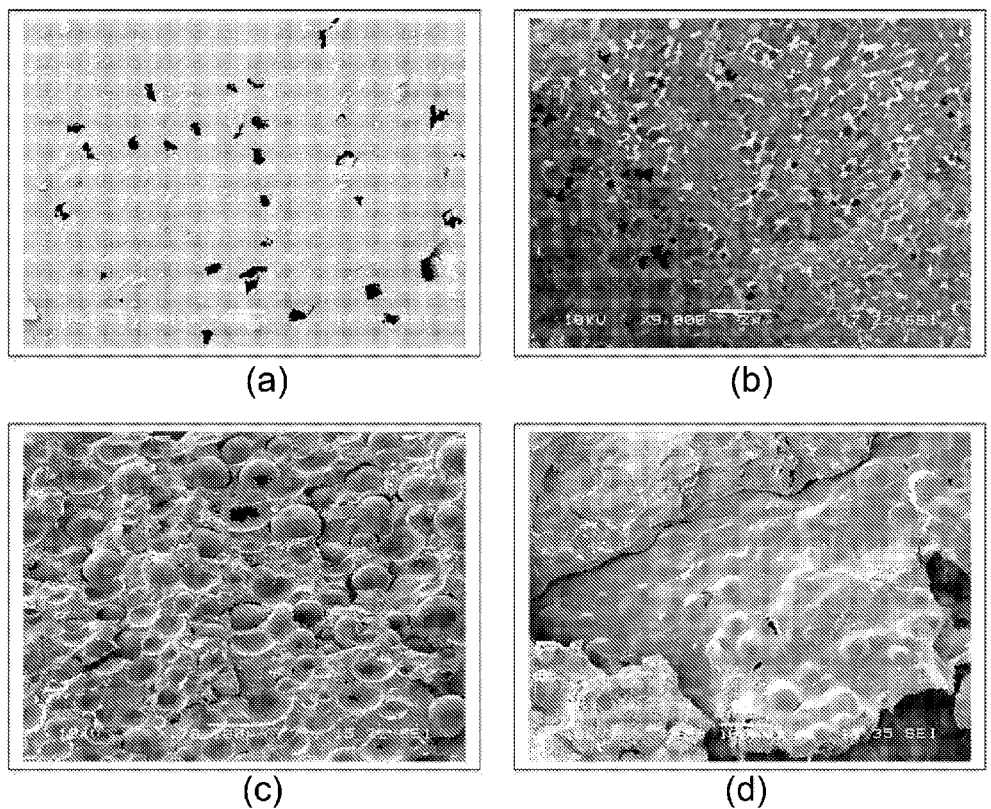
FIG. 22 shows secondary SEM micrographs of fracture surfaces after compression testing illustrating the morphology of the fracture surfaces of samples prepared with 30% $ZrO_2$ for cements containing (a) standard two-solution formulation (110X), (b) modified two-solution containing nanospheres (9000X), (c) modified two-solution containing microspheres (170X) and (d) KyphX at 30% $BaSO_4$ (150X), according to an embodiment of the present invention.

FIG. 22 shows secondary SEM micrographs of fracture surfaces after compression testing illustrating the morphology of the fracture surfaces of samples prepared with 30% $ZrO_2$ for cements containing (a) standard two-solution formulation (110X), (b) modified two-solution containing nanospheres (9000X), (c) modified two-solution containing microspheres (170X) and (d) KyphX at 30% $BaSO_4$ (150X). The nanospheres-containing cement interface is shown at higher magnification in comparison to the other micrographs in order to reveal the nanostructures apparent in the matrix.

The interfaces of the standard two solution formulation (a) showed a very smooth mirror-like zone. The fracture surface presented striated areas, which may be an indication of slow stable crack growth. The fracture surface of modified two-solution cement containing nanospheres (b) showed a rough interface. At higher magnifications it is possible to observe a homogeneous nanobeads-matrix structure. Internal cracks propagated in direction to the edge of the sample and not preferentially towards or surrounding beads. Presence of white regions surrounding beads indicates presence of radiopacifier distributed in the matrix. Fracture surfaces of modified standard two-solution cements containing microspheres (c) showed a rougher and grittier appearance. Microspheres embedded in the matrix are clearly seen, the removal of these microspheres created pores in the 50-100 µm range. Voids and microcracks also surrounded the PMMA particles where cracks seemed to grow preferentially through this region. The fracture surface of KyphX (d) presented a very rough and chalky appearance, due to $BaSO_4$ agglomerates, indicating zones with slow crack propagation and crack arrest. The incidence of cracks seems not to increase or decrease with an increasing concentration of radiopacifier for all the formulations evaluated in this study. In addition, the matrices of cements containing nanospheres and microspheres had homogeneous appearance with no substantial clumping of radiopacifier, as shown by the SEM micrographs illustrated in FIG. 20.

Example 18

Viscosity Measurements

This Example describes static viscosity measurements performed in order to evaluate the effect of addition of increasing contents of $ZrO_2$ on the rheological behavior of two-solution formulations. The flow behavior is an important parameter to consider since the actual viscosity of the standard formulation at a P:M 0.9:1 ratio is high for a relatively low polymer-to-monomer ratio. For this reason, cements containing cross-linked particles were designed (as described herein) in an attempt to increase the polymer-to-monomer ratio without subsequently increasing the viscosity of the solutions.

Briefly, the effect of $ZrO_2$ addition in increasing concentrations on the static viscosity of the three cement formulations were evaluated. Rheological measurements were performed with a Brookfield viscometer (DV-E Digital Viscometer) operated with a coaxial spindle and controllable speeds. Measurements were taken at increasing shear rates depending on the viscosity range of each formulation. The cements tested were prepared as described previously. Three measurements of each composition were performed at each shear rate and the average viscosity and standard deviation are reported. Two-way ANOVA with simple effects analysis was performed at a level of significance of 95% to determine the effect of cement composition and radiopacifier concentration on the viscosity behavior.

Figure 23:
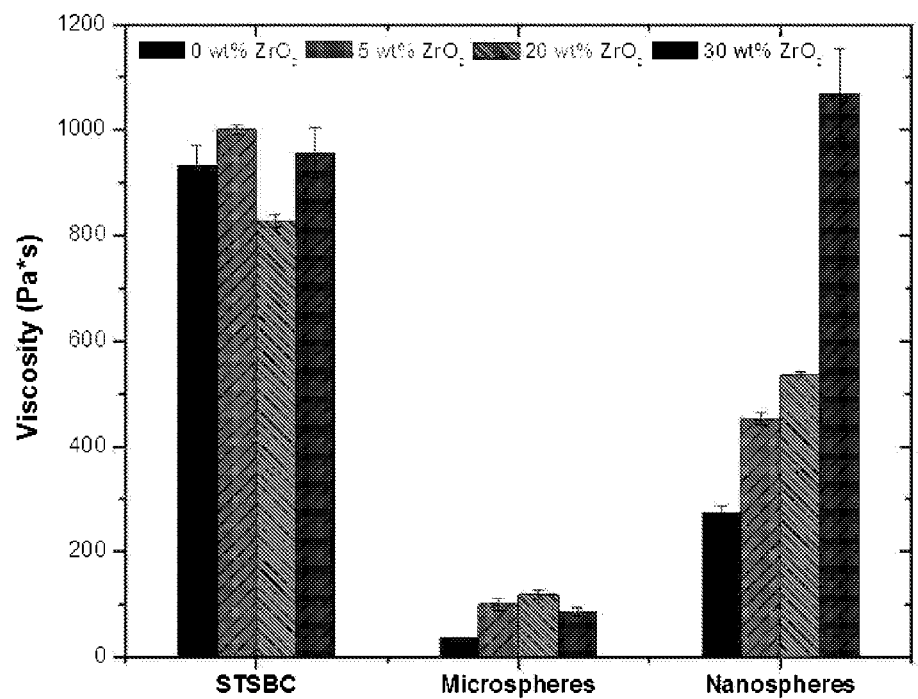
FIG. 23 shows the effect of radiopacifier on the viscosity of cements prepared with STSBC, microspheres and nanospheres, according to an embodiment of the present invention.

FIG. 23 shows the effect of radiopacifier on the viscosity of cements prepared with STSBC, microspheres and nanospheres. Comparison was performed at fixed shear rate (4 $s^{-1}$). The results show that the viscosity decreased (at 0% $ZrO_2$) with the addition of cross-linked particles in the cement matrix. Viscosity of cements containing microspheres and nanospheres were significantly lower than the viscosity of the standard two-solution cements (p<0.05).

It is evident from FIG. 23 that there is an effect of radiopacifier on the viscous flow of two-solution cements. Viscosity data is compared at a fixed shear rate (4 $s^-$) for all the three cement compositions. Comparing the three cements in the absence of radiopacifier, it is clear that the viscosity of the solutions decreases with the addition of cross-linked particles. The two-solution cements containing microspheres at 0% $ZrO_2$ showed very low viscosity; indeed the runny nature of this cement would not make it suitable for VP and KP applications due to possible extravasation from the vertebral body. When compared to the STSBC formulation (fixed shear rate of 4 $s^{-1}$), it is shown that the presence of cross-linked microspheres reduced viscosity by about 96% at a P:M 1:1 with $P_b:P_l$ 1.5:1 ratio. Cements prepared with cross-linked nanospheres showed higher viscosity than cements containing microspheres. In the absence of radiopacifier the viscosity is about 14% higher than the viscosity measured for microspheres-containing cements; however it is still 70% lower than the initial viscosity of STSBC. The addition of radiopacifier in microspheres-containing cements increased viscosity; however this increase is not significant across $ZrO_2$ concentrations (p>0.05) (the only significant difference was observed between 0 and 20% $ZrO_2$). On the contrary, the addition of increasing concentrations of radiopacifier significantly increased the viscosity (p<0.05) of cements prepared with nanospheres (p<0.05) and significantly affected the STSBC formulation (p<0.05) (except there is no significant difference between 0 and 30 and 5 and 30% $ZrO_2$). There is a significant difference among viscosities of the three cement formulations compared at 0, 5, 20 and 30% $ZrO_2$ (p<0.05). Simple effects analysis confirmed that the highest viscosity was achieved with nanospheres-containing cement at 30% $ZrO_2$ 1046 Pa*s), followed by STSBC at 5% $ZrO_2$ (1006 Pa*s). The lowest viscosity was measured for micropsheres-cements at 0% $ZrO_2$ (35.78 Pa*s).

The substantial increase in viscosity of nanospheres-containing cements in comparison to microspheres at all $ZrO_2$ concentrations is a result of the increased surface area of the beads, which enhances diffusion of the monomer in the particles, and increased volume fraction of particles in the cement mixture. At 30% $ZrO_2$, the nanospheres-containing cements showed difficult handling and slow mixing through a static mixing nozzle, making it unsuitable for delivery with a needle or cannula. On the other hand, at 20% the cement mixed well in the nozzle, making it possible to deliver with a 12G needle. These viscosity results give a range of compositions suitable for application in the treatment of vertebral compression fractures. Cements containing microspheres can be prepared with high radiopacifier concentrations, while cements containing nanospheres can be prepared with concentrations as high as 20%. Compression tests revealed that the standard formulation containing radiopacifier falls below the minimum ASTM requirement, and combined with the fact that the viscosity of the dough is considerably high it can be concluded that this composition is not adequate for the application discussed herein.

Example 19

Exothermal Testing

This Example describes the measurement of maximum temperatures and setting times for the three different cement types (modified two-solution bone cements with microspheres and nanospheres and the standard solution, described in the previous Examples) containing 0 and 20% $ZrO_2$ in order to discern possible effects of the addition of high concentrations of radiopacifier on the setting characteristics of these cement preparations. As discussed herein, the standard two-solution bone cement has a maximum polymerization exotherm around 100° C. and setting time of about 8 minutes.

Briefly, the exothermal polymerization temperatures and setting times of two-solution cements containing 20% $ZrO_2$ were measured, according to ASTM standard F451 (denominated standard mold, as should be appreciated by those skilled in the art), and compared to the respective formulation containing no radiopacifier added. A smaller custom-designed PTFE mold comprising a total volume of 3 cubic centimeters (denominated 3CC) was also used to measure the setting characteristics of the cements with the goal of replicating the approximate volume of cement delivered into a vertebral body during vertebroplasty. The maximum exotherm is defined as the peak in the temperature versus time curve during polymerization, while setting time is given by the time corresponding to the average temperature between ambient and maximum temperatures. Maximum temperatures and setting times are reported as the average of three measurements of each composition in both molds. Differences in the maximum exotherm and setting times of the three cement compositions prepared with 0 and 20% $ZrO_2$ were statistically analyzed applying two-way ANOVA with simple effects and Tukey post hoc (for the parameters that did not show significant interaction) at a level of significance of 95%.

Figure 24:
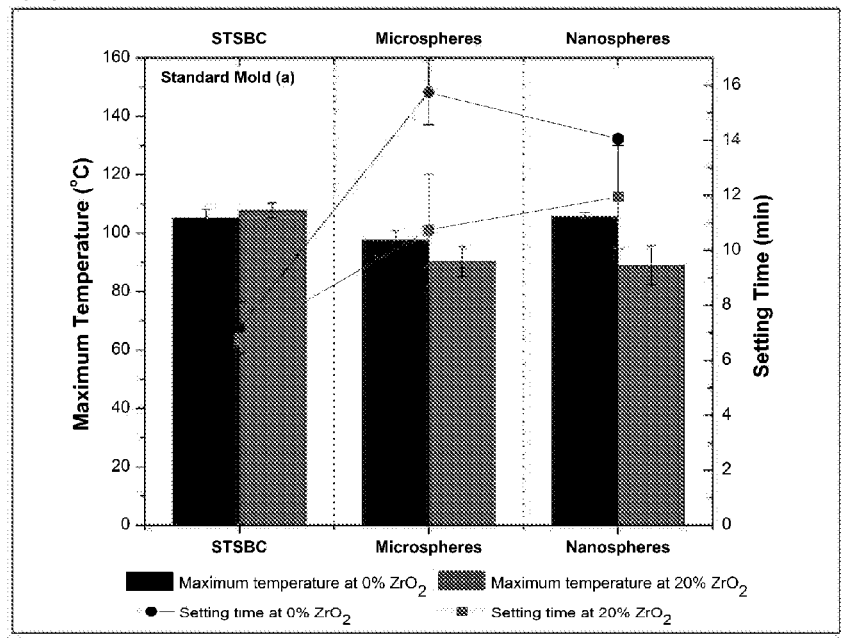
FIG. 24 shows the setting characteristics of cements prepared with nanospheres and microspheres compared at 0 and 20% $ZrO_2$; (a) shows the results obtained with the standard mold, and (b) shows the results obtained with the 3CC mold, according to an embodiment of the present invention.
Figure 24:
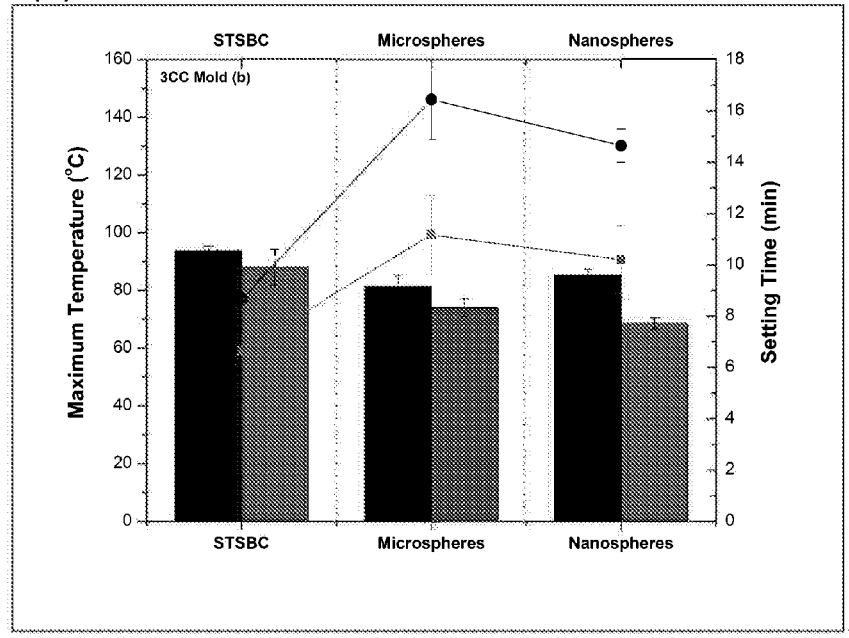

FIG. 24 shows the setting characteristics of cements prepared with nanospheres and microspheres compared at 0 and 20% $ZrO_2$; (a) shows the results obtained with the standard mold, and (b) shows the results obtained with the 3CC mold. Bars indicate maximum polymerization temperatures and lines and symbols setting times.

As noted, FIG. 24 illustrates the effect of the addition of radiopacifier in the exothermal and setting behavior of standard two-solution, nanospheres and microspheres-containing cements for experiments performed in the standard (a) and custom designed molds (b). It is evident from FIG. 24 (a) that in the absence of radiopacifier cements prepared with nanospheres presented maximum exotherm in the range of the standard formulation, while microsphere-containing cements showed lower temperature ($p<0.05$) than the standard formulation. However, the setting times of these cements were significantly increased in comparison to STSBC ($p<0.05$) (using the same initiation chemistry 1.25 g BPO/100 mL MMA and 0.7 mL/100 mL MMA). The addition of 20% $ZrO_2$ produced a significant decrease in maximum exotherm in nanospheres and microspheres cements ($p<0.05$) but not with the standard formulation ($p>0.05$). This decrease was about 10° C. in the maximum polymerization temperature of microspheres and about 15° C. for nanospheres-containing cements. The addition of 20% $ZrO_2$ decreased the setting time of microspheres cements significantly ($p<0.05$) with a reduction of more than 5 minutes; there was also a reduction in setting time for nanospheres-containing cements (about 3 minutes), although not statistically significant. The addition of radiopacifier did not affect the setting time of the STSBC ($p>0.05$). The average maximum temperature of STSBC cement is significantly higher ($p<0.05$) than nanospheres and microspheres-containing cements, both of which did not present significant differences in maximum exotherm ($p>0.05$). Similarly, STSBC had the lowest setting time ($p<0.05$) compared to microspheres and nanospheres cements, which did not show significant differences in setting time ($p<0.05$).

A similar trend is shown in the maximum exotherms obtained with the 3CC mold. However, there is no indication of interaction between cement type and $ZrO_2$ composition in setting time ($p>0.05$) measured with the smaller mold. Nonetheless, Tukey post hoc tests confirmed that STSBC had the lowest setting time ($p<0.05$) compared to microspheres and nanospheres cements, which did not show significant differences between setting times ($p<0.05$). A decrease of more than 15° C. in the maximum exotherm was measured with the custom-designed mold as compared to the results measured with the standard; however this is an expected result due to the smaller volume of cement surrounding the thermocouple.

The reduction in maximum temperature with the addition of 20% $ZrO_2$ in cements containing nanospheres and microspheres may be associated with the dissipation of energy by the $ZrO_2$ particles in combination with the cross-linked PMMA beads. Since there was no effect of the addition of radiopacifier in the standard-two solution cement ($p>0.05$), which is solely composed of linear polymer, it could be concluded that nanospheres and microspheres acted as an insulator phase in the cements matrix, thereby absorbing and dissipating the excess heat generated during curing of the cement.

The addition of radiopacifier decreased the setting times of cements prepared with cross-linked particles. It is discussed herein that in the absence of radiopacifier the setting time of cements prepared with cross-linked microspheres and nanospheres was longer than that of the standard formulation. The reason for this increase in setting time may be associated with the fact that cross-linked particles swell in monomer, therefore leaving larger amounts of free monomer available in the matrix, which consequently, slow the polymerization process. Thus, when the radiopacifier was added to the cement mixture containing cross-linked particles, the available monomer quickly wetted the $ZrO_2$ particles accelerating polymerization. Even though the setting time of the modified two-solution cements decreased with higher contents of $ZrO_2$, this reduction should not compromise cement injection and handling and, therefore the application in KP and VP. Cements containing high concentration of radiopacifier and nanospheres or microspheres showed appropriate curing properties for applications in the treatment of compression fractures.

The previous eight Examples examined the effect of high concentrations of $ZrO_2$ on the static mechanical properties, porosity and fracture mode, viscosity and curing parameters of novel two-solution cements. The results confirmed the viability of preparing modified two-solution cements containing elevated content of radiopacifier tuned for enhanced visualization under fluoroscopy without degrading the mechanical properties of the material. These cements presented matrices without significant evidence of macroporosity and clumping of the contrast agent, which led to an increase in compressive strength with increasing content of $ZrO_2$. The viscosity of these cements is appropriate as well as the maximum polymerization exotherm and setting times.

While several embodiments of the invention have been discussed, it will be appreciated by those skilled in the art that various modifications and variations of the present invention are possible. Such modifications do not depart from the spirit and scope of the claimed invention.

What is claimed is:
1. An orthopedic bone cement comprising:
cross-linked polymer beads, wherein said cross-linked beads comprise cross-linked poly(methyl methacrylate) (PMMA) beads, wherein a surface of each of said cross linked beads comprise functional reactive sites, and wherein said functional reactive sites comprise carbon-carbon double bonds, wherein said cross-linked PMMA beads comprising said functional reactive sites comprise the following formula:

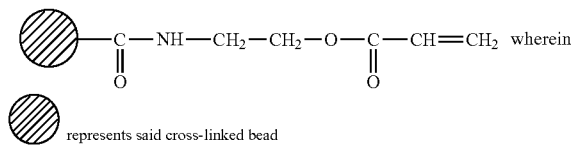

represents said cross-linked bead;
a linear polymer, wherein said cross-linked polymer beads and said linear polymer comprise total polymer; and
a monomer, wherein total polymer to monomer ratio is between about 1:1 g/ml and 1.4:1 g/ml, and cross-linked polymer bead to linear polymer ratio is between about 1:1 g/g and 2:1 g/g.

2. The orthopedic bone cement of claim 1, wherein the total polymer to monomer ratio is between about 1:1 and 1.2:1.

3. The orthopedic bone cement of claim 1, wherein the total polymer to monomer ratio is between about 1:1 and 1.1:1.

4. The orthopedic bone cement of claim 3, wherein the cross-linked polymer beads to linear polymer ratio is between about 1:1 and 1.5:1.

5. The orthopedic bone cement of claim 4, wherein said linear polymer comprises poly(methyl methacrylate) (PMMA).

6. The orthopedic bone cement of claim 5, wherein said cross-linked polymer beads comprise cross-linked poly(methyl methacrylate) (PMMA) beads.

7. The orthopedic bone cement of claim 6, wherein said wherein said monomer comprises methyl methacrylate monomer (MMA).

8. The orthopedic bone cement of claim 7, wherein said cross-linked poly(methyl methacrylate) (PMMA) beads comprise microspheres sized between about 20 to 100 micrometers.

9. The orthopedic bone cement of claim 8, further comprising a radiopaque material.

10. The orthopedic bone cement of claim 9, wherein said radiopaque material comprises $ZrO_2$.

11. The orthopedic bone cement of claim 10, wherein said $ZrO_2$ content is about 5% to 30% by weight.

12. The orthopedic bone cement of claim 7, wherein said cross-linked poly(methyl methacrylate) (PMMA) beads comprise nanospheres sized between about 300 to 330 nanometers.

13. The orthopedic bone cement of claim 11, wherein said $ZrO_2$ content is about 5% to 20% by weight.

14. The orthopedic bone cement of claim 13, wherein said $ZrO_2$ content is about 20% by weight.

* * * * *